US008349312B2

(12) United States Patent
Wang et al.

(10) Patent No.: US 8,349,312 B2
(45) Date of Patent: Jan. 8, 2013

(54) PROLINE SUBSTITUTED CYCLOSPORIN ANALOGUES

(75) Inventors: Guoqiang Wang, Belmont, MA (US); Yat Sun Or, Watertown, MA (US); Jiang Long, Wayland, MA (US); Xuri Gao, Newton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 199 days.

(21) Appl. No.: 12/832,383

(22) Filed: Jul. 8, 2010

(65) Prior Publication Data
US 2011/0008286 A1  Jan. 13, 2011

Related U.S. Application Data

(60) Provisional application No. 61/224,343, filed on Jul. 9, 2009.

(51) Int. Cl.
*A61K 38/21* (2006.01)

(52) U.S. Cl. ...................................................... 424/85.4

(58) Field of Classification Search .................. None
See application file for complete search history.

(56) References Cited

U.S. PATENT DOCUMENTS

| | | | |
|---|---|---|---|
| 4,108,985 A | 8/1978 | Ruegger et al. | |
| 4,220,641 A | 9/1980 | Traber et al. | |
| 4,288,431 A | 9/1981 | Traber et al. | |
| 4,384,996 A | 5/1983 | Bollinger et al. | |
| 4,396,542 A | 8/1983 | Wenger | |
| 4,554,351 A | 11/1985 | Wenger | |
| 4,771,122 A | 9/1988 | Seebach | |
| 4,798,823 A | 1/1989 | Witzel | |
| 5,239,057 A | 8/1993 | Wang et al. | |
| 5,284,826 A | 2/1994 | Eberle | |
| 5,525,590 A | 6/1996 | Bollinger et al. | |
| 5,604,092 A | 2/1997 | Erlanger et al. | |
| 6,784,156 B2 | 8/2004 | Or et al. | |
| 6,790,935 B1 * | 9/2004 | Mutter et al. | 530/317 |
| 6,809,077 B2 | 10/2004 | Or et al. | |
| 6,979,671 B2 | 12/2005 | Or et al. | |
| 7,012,064 B2 | 3/2006 | Or et al. | |
| 7,012,065 B2 | 3/2006 | Or et al. | |
| 7,468,419 B2 | 12/2008 | Wu et al. | |
| 2002/0142946 A1 | 10/2002 | Or et al. | |
| 2003/0087813 A1 | 5/2003 | Or et al. | |
| 2003/0104992 A1 | 6/2003 | Or et al. | |
| 2006/0069015 A1 | 3/2006 | Molino et al. | |
| 2007/0213301 A1 | 9/2007 | Zhang et al. | |
| 2007/0249547 A1 | 10/2007 | Olson et al. | |
| 2010/0196316 A1 | 8/2010 | Or et al. | |
| 2010/0209390 A1 | 8/2010 | Or et al. | |
| 2011/0008284 A1 | 1/2011 | Gao et al. | |
| 2011/0008285 A1 | 1/2011 | Long et al. | |
| 2011/0206637 A1 | 8/2011 | Or et al. | |
| 2011/0218175 A1 | 9/2011 | Or et al. | |

FOREIGN PATENT DOCUMENTS

| | | |
|---|---|---|
| EP | 0034567 A2 | 8/1981 |
| EP | 0056782 A1 | 7/1982 |
| EP | 0300784 A2 | 1/1989 |
| EP | 0300785 A2 | 1/1989 |
| GB | 2206119 A | 12/1988 |
| GB | 2207678 A | 2/1989 |
| WO | 8602080 A1 | 4/1986 |
| WO | 9918120 A1 | 4/1999 |
| WO | 03033526 A2 | 4/2003 |
| WO | 2005021028 A1 | 3/2005 |
| WO | 2006005610 A1 | 1/2006 |
| WO | 2006038088 A1 | 4/2006 |
| WO | 2006039668 A2 | 4/2006 |
| WO | 2007041631 A1 | 4/2007 |
| WO | 2007049803 A1 | 5/2007 |
| WO | 2007112345 A2 | 10/2007 |
| WO | 2007112352 A2 | 10/2007 |
| WO | 2007112357 A2 | 10/2007 |
| WO | 2008139986 A1 | 11/2008 |
| WO | 2012009715 A2 | 1/2012 |
| WO | 2012021796 A2 | 2/2012 |

OTHER PUBLICATIONS

Nakagawa, M., et al., "Suppression of Hepatitis C Virus Replication by Cyclosporin A is Mediated by Blockade of Cyclophilins", Gastroenterology 2005, 129:1031-1041.

Traber, R. and Dreyfuss, MM, "Occurrence of cyclosporins and cyclosporin-like peptolides in fungi", Journal of Industrial Microbiology (1996) 17:397-401.

Kobel, et al., "Directed Biosynthesis of Cyclosporins," Europ. J. Applied Microbiology and Biotechnology, 14:273-240, 1982.

Von Wartburg, et al., "Chemistry of the Natural Cyclosporin Metabolites", Progress in Allergy, 38:28-45, 1986.

Wenger, R., "Synthesis of Cyclosporine and Analogues: Structure, Activity, Relationships of New Cycloporine Derivatives", Transpl. Proc., XV(4):Suppl. 1, pp. 2230-2241, 1983.

Wenger, "Cyclosporine and Analogues—Isolation and Synthesis—Mechanism of Action and Structural Requirements for Pharmacological Activity," Progress in the Chemistry of Organic Natural Products, 50:123-168, 1986.

Watashi et al., "Cyclosporin A Suppresses Replication of Hepatitis C Virus Genome in Cultured Hepatocytes," Hepatology, 38(5):1282-1288, 2003.

Nakagawa et al., "Specific Inhibition of Hepatitis C Virus Replication by Cyclosporin A", Biochem. Biophys. Res. Commun., 313:42-47, 2004.

Shimotohno, et al., "Inhibitory Role of Cyclosporin A and Its Derivatives on Replication of Hepatitis C Virus", American Transplant Congress, Abstract No. 648 (American Journal of Transplantation) pp. 1+2, 2004. (Abstract only).

Inoue, et al., "Combined Interferon α2b and Cyclosporin A in the Treatment of Chronic Hepatitis C: Controlled Trial", Journal of Gastroenterology, 38:567-572, 2003.

(Continued)

Primary Examiner — Marcela M Cordero Garcia
Assistant Examiner — Kaipeen Yang
(74) Attorney, Agent, or Firm — Elmore Patent Law Group, P.C.; Edgar W. Harlan; Carolyn S. Elmore, Esq.

(57) ABSTRACT

The present invention provides novel proline substituted cyclosporinanalogue compounds, pharmaceutical compositions comprising these compounds and methods of using these compounds for the treatment of disorders and diseases, including immune disorders, inflammatory disorders and viral infections.

18 Claims, No Drawings

OTHER PUBLICATIONS

Paeshuyse, et al., "Potent and Selective Inhibition of Hepatitis C Virus Replication by the Non-Immunosuppressive Cyclosporin Analogue DEBIO-025," Abstract 28:A41, 2005. (Abstract only).

Flisiak, R., et al., "The Cyclophilin Inhibitor Debio-025 Shows Potent Anti-Hepatitis C Effect in Patients Coinfected with Hepatitis C and Human Immunodeficiency Virus", Hepatology, 47(3):817-826, 2008.

Papageorgiou, C., et al., "Improved Binding Affinity for Cyclophilin A by a Cyclosporin Derivative Singly Modified at Its Effector Domain", J. Med. Chem. 37:3674-3676, 1994.

Ma, S., et al., "NIM811, a Cyclophilin Inhibitor, Exhibits Potent In Vitro Activity against Hepatitis C Virus Alone or in Combination with Alpha Interferon", Antimicrobial Agents and Chemotherapy, 50(9):2976-2982, Sep. 2006.

Robida, J.M., et al., "Characterization of Hepatitis C Virus Subgenomic Replicon Resistance to Cyclosporine in Vitro", Journal of Virology, 81(11):5829-5840, 2007.

Flisiak, R., et al., "Cyclophilin Inhibitors in Hepatitis C Viral Infection", Expert Opin. Investig. Drugs, 16(9):1345-1354, 2007.

Papageorgiou, C., et al., "Calcineurin Has A Very Tight-Binding Pocket for the Side Chain of Residue 4 of Cyclosporin", Bioorganic & Medicinal Chemistry Letters, 4(2):267-272, 1994.

Freidinger, R.M., et al., "Synthesis of 9-Fluorenylmethyloxycarbonyl-Protected N-Alkyl Amino Acids by Reduction of Oxazolidinones", J. Org. Chem., 48:77-81, 1983.

* cited by examiner ns developed by R. Wenger—see e.g. Traber et al., 1; Traber et al., 2; and Kobel et al., loc cit. U.S. Pat. Nos. 4,108,985, 4,220,641, 4,288,431, 4,554,351, 4,396,542 and 4,798,823; European Patent Publication Nos. 34,567A, 56,782A, 300, 784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 24 77 (1985) and Wenger 3, Progress in the Chemistry of Organic Natural Products, 50, 123 (1986). Several synthetic modifications of the—MeBmt-residue residing at position 1 of the cyclosporin undecapeptide have been described including: Park et al., *Tetrahedron Lett.* 1989, 30, 4215-4218; U.S. Pat. Nos. 5,239, 037, 5,293,057; U.S. Publication Nos. US20020142946, US20030087813, and US20030104992 assigned to Enanta Pharmaceuticals, Inc.; PCT Publication Nos. WO99/18120 and WO03/033526 both assigned to Isotechnika; and U.S. Pat. Nos. 4,384,996, 4,771,122, 5,284,826, and 5,525,590 assigned to Sandoz.

PROLINE SUBSTITUTED CYCLOSPORIN ANALOGUES

RELATED APPLICATION

This application claims the benefit of U.S. Provisional Application No. 61/224,343, filed on Jul. 9, 2009. The entire teachings of the above application are incorporated herein by reference.

TECHNICAL FIELD

The present invention relates to novel cyclosporin analogues, compositions containing them, processes for their preparation, intermediates in their synthesis, and their use as therapeutics for prevention of organ transplantation rejection, the treatment of immune disorders and inflammation, and treatment of viral (particularly heptitis C viral) infection.

BACKGROUND OF THE INVENTION

Cyclosporin A (CsA), a neutral cyclic undecapeptide isolated from the fungus *Tolypocladium injlaturn* and currently marketed as Neoral and sandimmunem (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Since the original discovery of cyclosporin, a wide variety of naturally occurring cyclosporins have been isolated and identified, and many further nonnatural cyclosporins have been prepared by total- or semi-synthetic means or by the application of modified culture techniques. The class comprised by the cyclosporins is thus now substantial and includes, for example, the naturally occurring cyclosporins A through Z [cf., Traber et al.; 1, Helv. Chim. Acta, 60, 1247-1255 (1977); Traber et al.; 2, Helv. Chim. Acta, 65, 1655-1667 (1982); Kobel et al.; Europ. J. Applied Microbiology and Biotechnology, 14, 273-240 (1982); and von Wartburg et al.; Progress in Allergy, 38, 28-45 (1986)], as well as various non-natural cyclosporin derivatives and artificial or synthetic cyclosporin derivatives and artificial or synthetic cyclosporins including dihydrocyclosporins [in which the—MeBmt-residue is saturated by hydrogenation]; derivatized cyclosporins (e.g., in which the 3'—O-atom of the—MeBmt-residue is acylated or a further substituent is introduced at the a-carbon atom of the sarcosyl residue at the 3-position); and cyclosporins in which variant amino acids are incorporated at specific positions within the peptide sequence, e.g. employing the total synthetic method for the production of cyclosporins The compound cyclosporin (cyclosporinA or CsA) has found wide use since its introduction in the fields of organ transplantation and immunomodulation, and has brought about a significant increase in the success rate for transplantation procedures. Undesired side effects associated with cyclosporin, however, such as nephrotoxicity, have led to a continued search for immunosuppressant compounds having improved, efficacy and safety.

Side effects with systemic CsA include increase in diastolic blood pressure and decrease in renal function. Other side effects include hepatic dysfunction, hypertrichosis, tremor, gingival hyperplasia and paraesthsia. The systemic toxicity of CsA limits its use for the treatment of certain diseases. Accordingly, a need exists for compounds which exhibit immunosuppressive activity while not producing systemic toxicity.

Cyclosporin A and certain derivatives have been reported as having anti-HCV activity, see Watashi et al., Hepatology, 2003, Volume 38, pp 1282-1288, Nakagawa et al., Biochem. Biophys. Res. Commun. 2004, Volume 3 13, pp 42-7, and Shimotohno and K. Watashi, 2004 American Transplant Congress, Abstract No. 648 (American Journal of Transplantation 2004, Volume 4, Issue s8, Pages 1-653). The authors of the Nakagawa et al. paper state that certain chaperone activities, such as those of cyclophilins, may be crucial for the processing and maturation of the viral proteins and for viral replication. Cyclosporin derivatives having anti-HCV activity are known from International Publication Nos. WO 2005/021028, WO 2006/039668, WO 2006/038088, WO 2006/039688, WO 2007/112352, WO 2007/112357, WO 2007/112345 and WO 2007/041631.

A subsequent controlled clinical trial showed that a combination of cyclosporin A with interferon α2b is more effective than interferon monotherapy, especially in patients with high viral loads (Inoue et al., "Combined Interferon α2b and Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporine for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Debio-025 does possess potent binding affinity for cyclophilin A.

SUMMARY OF THE INVENTION

The present invention relates to novel cyclosporin analogues represented herein below, pharmaceutical compositions comprising such compounds, methods for the treatment of viral (particularly hepatitis C viral) infection in a subject in need of such therapy with said compounds and methods of treatment for prevention of organ transplantation rejection, the treatment of immune disorders and inflammation.

In its principal embodiment, the present invention provides a compound of formula (I);

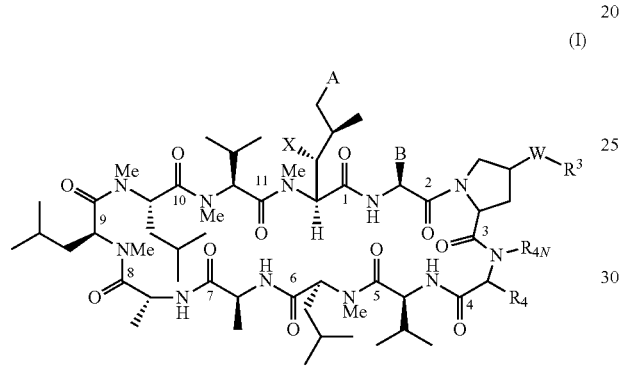

(I)

where:
A is

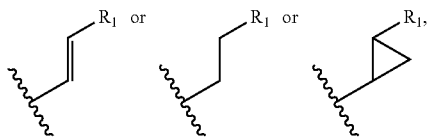

where, $R_1$ is selected from;
a) $R_{11}$, where $R_{11}$ is selected from;
  1) Hydrogen;
  2) Deuterium;
  3) $C_1$-$C_8$ alkyl;
  4) Substituted $C_1$-$C_8$ alkyl;
  5) $C_2$-$C_8$ alkenyl;
  6) Substituted $C_2$-$C_8$ alkenyl;
  7) $C_2$-$C_8$ alkynyl;
  8) Substituted $C_2$-$C_8$ alkynyl;
  9) $C_3$-$C_{12}$ cycloalkyl;
  10) Substituted $C_3$-$C_{12}$ cycloalkyl;
  11) Aryl;
  12) Substituted aryl;
  13) Heterocycloalkyl;
  14) Substituted heterocycloalkyl;
  15) Heteroaryl; and
  16) Substituted heteroaryl;
b) —C(O)O$R_{11}$, where $R_{11}$ is as previously defined;
c) —C(O)$R_{11}$, where $R_{11}$ is as previously defined;
d) —C(O)OCH$_2$—V—$R_{12}$, where V is —O— or —S— and $R_{12}$ is selected from;
  1) $C_1$-$C_8$ alkyl;
  2) Substituted $C_1$-$C_8$ alkyl;
  3) $C_2$-$C_8$ alkenyl;
  4) Substituted $C_2$-$C_8$ alkenyl;
  5) $C_2$-$C_8$ alkynyl;
  6) Substituted $C_2$-$C_8$ alkynyl;
  7) $C_3$-$C_{12}$ cycloalkyl;
  8) Substituted $C_3$-$C_{12}$ cycloalkyl;
  9) Aryl;
  10) Substituted aryl;
  11) Heterocycloalkyl;
  12) Substituted heterocycloalkyl;
  13) Heteroaryl; and
  14) Substituted heteroaryl;
e) —C(O)N($R_{13}$)($R_{14}$), where $R_{13}$ and $R_{14}$ are independently selected from $R_{11}$ and $R_{11}$ is as previously defined or $R_{13}$ and $R_{14}$ combined together with the N which attached to is substituted or unsubstituted heterocycloalkyl;
f) —C(O)S$R_{11}$, where $R_{11}$ is as previously defined;
g) —C(S)O$R_{11}$, where $R_{11}$ is as previously defined;
h) —C(O)OCH$_2$OC(O)$R_{12}$, where $R_{12}$ is as previously defined;
i) —C(S)S$R_{11}$, where $R_{11}$ is as previously defined; and
j) $R_{15}$, where $R_{15}$ is selected from;
  1) -M-$R_{11}$, where $R_{11}$ is as previously defined and M is selected from;
    i. $C_1$-$C_8$ alkyl;
    ii. Substituted $C_1$-$C_8$ alkyl;
    iii. $C_2$-$C_8$ alkenyl;
    iv. Substituted $C_2$-$C_8$ alkenyl;
    v. $C_2$-$C_8$ alkynyl;
    vi. Substituted $C_2$-$C_8$ alkynyl;
    vii. $C_3$-$C_{12}$ cycloalkyl; and
    viii. Substituted $C_3$-$C_{12}$ cycloalkyl;
  2) -M-N$R_{13}R_{14}$, where $R_{13}$, $R_{14}$ and M are as previously defined;
  3) -M-S(O)$_m R_{11}$, where m=0, 1, or 2; M and $R_{11}$ are as previously defined;
  4) -M-O$R_{11}$, where M and $R_{11}$ are as previously defined;
  5) -M-C(O)$R_{11}$, where M and $R_{11}$ are as previously defined;
  6) -M-OC(O)$R_{12}$, where M and $R_{12}$ are as previously defined;
  7) -M-OC(O)O$R_{12}$, where M and $R_{12}$ are as previously defined;
  8) -M-N$R_{17}$C(O)$R_{12}$, where $R_{17}$ is $R_{11}$, M and $R_{12}$ are as previously defined;
  9) -MN$R_{17}$C(O)O$R_{12}$, where $R_{17}$, M and $R_{12}$ are as previously defined;
  10) -M-C(O)N$R_{13}R_{14}$, where $R_{13}$, M and $R_{14}$ are as previously defined;
  11) -M-C(O)N($R_{17}$)—O$R_{11}$, where $R_{17}$, M and $R_{11}$ are as previously defined;
  12) -M-OC(O)N$R_{13}R_{14}$, where $R_{13}$, M and $R_{14}$ are as previously defined;
  13) -M-N$R_{17}$C(O)N$R_{16}R_{11}$, where M, $R_{13}$, $R_{17}$ and $R_{14}$ are as previously defined;
  14) -M-C(S)S$R_{11}$, where M and $R_{11}$ are as previously defined;
  15) -M-OC(S)S$R_{12}$, where M and $R_{12}$ are as previously defined;
  16) -M-N$R_{17}$C(O)S$R_{12}$, where M, $R_{17}$ and $R_{12}$ are as previously defined;

17) -M-SC(O)NR$_{13}$R$_{14}$, where M, R$_{13}$ and R$_{14}$ are as previously defined;
18) -M-CH=N—OR$_{11}$, where M and R$_{11}$ are as previously defined; and
19) -M-CH=N—NR$_{13}$R$_{14}$, where M, R$_{13}$ and R$_{14}$ are as previously defined;

B is ethyl, 1-hydroxyethyl, isopropyl or n-propyl;
X is OR$_1$ or SR$_1$, where R$_1$ is as previously defined;
W is absent, —O—, or —S(O)$_m$—, where m=0, 1, or 2;
R$_3$ is R$_1$, where R$_1$ is as previously defined;
R$_{4N}$ is selected from methyl, ethyl, allyl and propyl;
R$_4$ is —(CH$_2$)n$_1$-C(R$_{41}$)(R$_{42}$)—W$_1$—R$_1$, where n$_1$=0, 1 or 2; W$_1$ is absent, —O—, or —S(O)$_m$, where m=0, 1 or 2; R$_{41}$ and R$_{42}$ are independently selected from: hydrogen, methyl, ethyl, allyl, propyl and isopropyl; and R$_1$ is as previously defined.

In another embodiment, the present invention provides the use of cyclosporin analogs for the treatment of, with or without the concurrent use of other drugs, organ transplantation rejections, immune disorders, and inflammation including, but not limited to, indications such as rheumatoid arthritis, psoriasis, inflammatory bowel diseases, chronic obstructive pulmonary disease, allergic rhinitis, and asthma.

In yet another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In still another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

Yet another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of formula (I) as illustrated above, or a pharmaceutically acceptable salt, ester or prodrug thereof.

Representative subgenera of the present invention include:
Compounds of formula I which are represented by the formula (II):

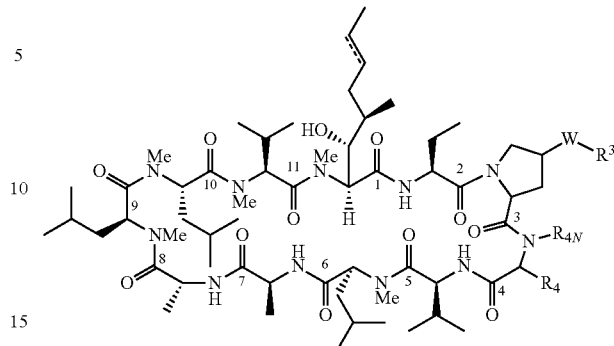

(II)

wherein R$_3$, R$_4$, R$_{4N}$ and W are as defined for formula I and ----- represents a single bond or a double bond.

Compounds of formula I which are represented by the formula (III):

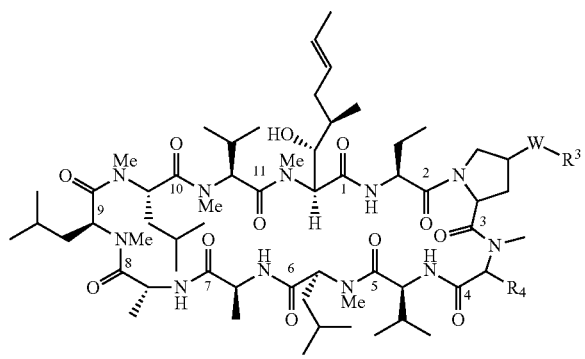

(III)

wherein R$_3$, R$_4$ and W are as defined for formula I.

Compounds or formula I which are represented by the formula (IV):

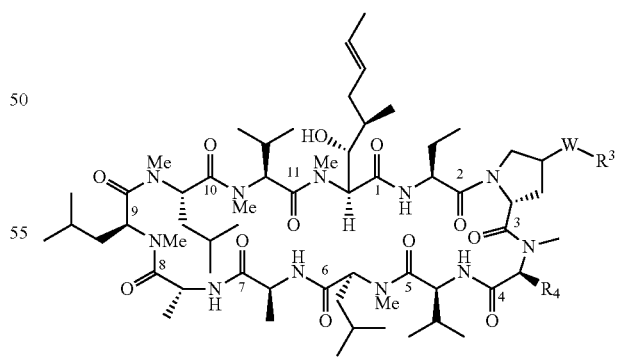

(IV)

wherein R$_3$, R$_4$ and W are as defined for formula I.
Representative species of the present invention include:
Example 1: Compound of formula IV: R$_4$=isobutyl, W is absent, and R$_3$=H;
Example 2: Compound of formula IV: R$_4$=isobutyl, W=O, and R$_3$=H;

Example 3: Compound of formula IV: $R_4$=isobutyl, W=O, and $R_3$=Me;

Example 4: Compound of formula IV: $R_4$=isobutyl, W=O, and $R_3$=Ac;

Example 5: Compound of formula IV: $R_4$=isobutyl, W=O, and $R_3$=allyl;

Example 6: Compound of formula IV: $R_4$=isobutyl, W=O, and $R_3$=—C(O)NH$_2$;

Example compounds 7-24 of the formula IV, wherein W, $R_4$ and $R_3$ are delineated for each example in Table I.

TABLE I

| Example | W | $R_4$ | $R_3$ |
|---|---|---|---|
| 7 | O | isobutyl | N,N-dimethylcarbamoyl |
| 8 | O | isobutyl | N,N-diethylcarbamoyl |
| 9 | O | isobutyl | aziridinylcarbonyl |
| 10 | O | isobutyl | azetidinylcarbonyl |
| 11 | O | isobutyl | pyrrolidinylcarbonyl |
| 12 | O | isobutyl | piperidinylcarbonyl |
| 13 | O | isobutyl | morpholinylcarbonyl |
| 14 | O | isobutyl | thiomorpholinylcarbonyl |
| 15 | O | isobutyl | thiomorpholinyl-S,S-dioxide carbonyl |
| 16 | O | isobutyl | piperazinylcarbonyl |
| 17 | O | isobutyl | 4-methylpiperazinylcarbonyl |
| 18 | O | isobutyl | 4-isopropylpiperazinylcarbonyl |
| 19 | O | isobutyl | cinnamyl |
| 20 | O | isobutyl | hydroxyethyl |
| 21 | O | isobutyl | carbamate |
| 22 | O | isobutyl | morpholinyl carbamate |
| 23 | O | isobutyl | piperidinyl carbamate |
| 24 | O | isobutyl | 4-methylpiperazinyl carbamate |

Example 25: Compound of formula IV: R$_4$=isopropyl, W=absent, and R$_3$=H.

Example compounds 25-185 of the formula IV, wherein W, R$_4$ and R$_3$ are delineated for each example in Table II.

TABLE II

| Example | W | R$_4$ | R$_3$ |
|---|---|---|---|
| 25 | absent | isopropyl | H |
| 26 | O | isopropyl | H |
| 27 | O | isopropyl | Ac |
| 28 | O | isopropyl | allyl |
| 29 | O | isopropyl | -C(CH$_3$)$_2$C(O)NH$_2$ |
| 30 | O | isopropyl | -C(CH$_3$)$_2$C(O)N(CH$_3$)$_2$ |
| 31 | O | isopropyl | -C(CH$_3$)$_2$C(O)N(Et)$_2$ |
| 32 | O | isopropyl | -C(CH$_3$)$_2$C(O)N(Et)$_2$ |
| 33 | O | isopropyl | -C(CH$_3$)$_2$C(O)-azetidinyl |
| 34 | O | isopropyl | -C(CH$_3$)$_2$C(O)-pyrrolidinyl |

TABLE II-continued

| Example | W | R₄ | R₃ |
|---|---|---|---|
| 35 | O | isopropyl-CH | -C(CH₃)-C(O)-N(piperidine) |
| 36 | O | isopropyl-CH | -C(CH₃)-C(O)-N(morpholine) |
| 37 | O | isopropyl-CH | -C(CH₃)-C(O)-N(thiomorpholine) |
| 38 | O | isopropyl-CH | -C(CH₃)-C(O)-N(thiomorpholine-S,S-dioxide) |
| 39 | O | isopropyl-CH | -C(CH₃)-C(O)-N(piperazine)-NH |
| 40 | O | isopropyl-CH | -C(CH₃)-C(O)-N(4-methylpiperazine) |
| 41 | O | isopropyl-CH | -C(CH₃)-C(O)-N(4-isopropylpiperazine) |
| 42 | O | isopropyl-CH | -CH(CH₃)-CH=CH-C₆H₅ |
| 43 | O | isopropyl-CH | -CH(CH₃)-CH₂-CH₂-OH |
| 44 | O | isopropyl-CH | -CH(CH₃)-CH₂-CH₂-O-C(O)-NH₂ |

TABLE II-continued
| Example | W | R4 | R3 |
|---|---|---|---|
| 45 | O |  | 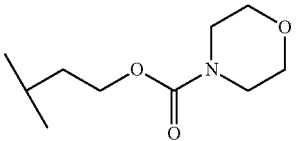 |
| 46 | O |  | 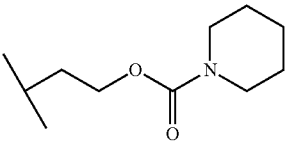 |
| 47 | O |  | 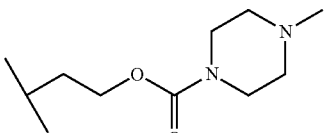 |
| 48 | absent | 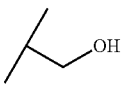 | H |
| 49 | O | 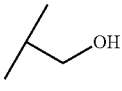 | H |
| 50 | O | 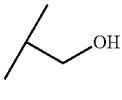 | Ac |
| 51 | O | 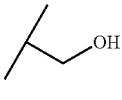 | allyl |
| 52 | O | 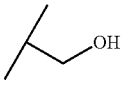 | 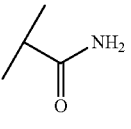 |
| 53 | O | 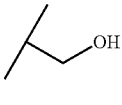 | 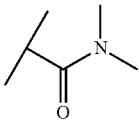 |
| 54 | O | 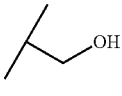 | 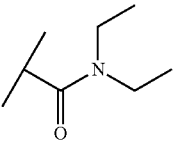 |
| 55 | O | 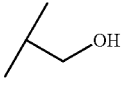 | 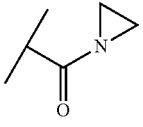 |

TABLE II-continued

| Example | W | R₄ | R₃ |
|---|---|---|---|
| 56 | O | CH(CH₃)CH₂OH | C(CH₃)-C(O)-azetidin-1-yl |
| 57 | O | CH(CH₃)CH₂OH | C(CH₃)-C(O)-pyrrolidin-1-yl |
| 58 | O | CH(CH₃)CH₂OH | C(CH₃)-C(O)-piperidin-1-yl |
| 59 | O | CH(CH₃)CH₂OH | C(CH₃)-C(O)-morpholin-4-yl |
| 60 | O | CH(CH₃)CH₂OH | C(CH₃)-C(O)-thiomorpholin-4-yl |
| 61 | O | CH(CH₃)CH₂OH | C(CH₃)-C(O)-(1,1-dioxo-thiomorpholin-4-yl) |
| 62 | O | CH(CH₃)CH₂OH | C(CH₃)-C(O)-piperazin-1-yl |
| 63 | O | CH(CH₃)CH₂OH | C(CH₃)-C(O)-(4-methylpiperazin-1-yl) |
| 64 | O | CH(CH₃)CH₂OH | C(CH₃)-C(O)-(4-isopropylpiperazin-1-yl) |

TABLE II-continued
| Example | W | R₄ | R₃ |
|---|---|---|---|
| 65 | O | 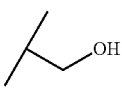 | 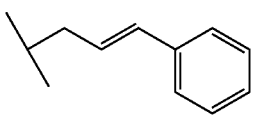 |
| 66 | O | 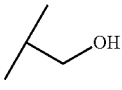 | 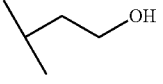 |
| 67 | O | 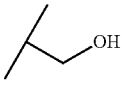 | 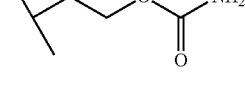 |
| 68 | O | 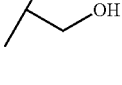 | 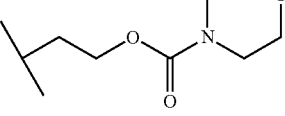 |
| 69 | O | 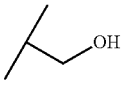 | 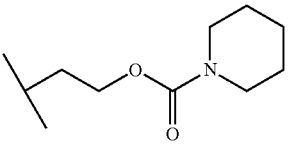 |
| 70 | O | 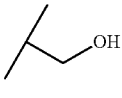 | 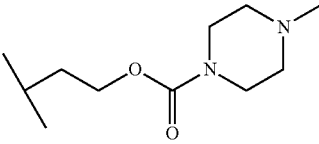 |
| 71 | absent | 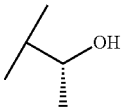 | H |
| 72 | O | 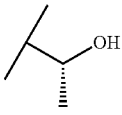 | H |
| 73 | O | 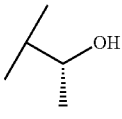 | Ac |
| 74 | O | 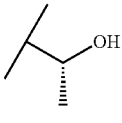 | allyl |
| 75 | O | 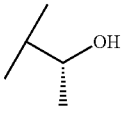 | 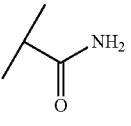 |
| 76 | O | 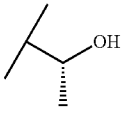 | 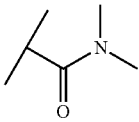 |

TABLE II-continued

| Example | W | R₄ | R₃ |
|---|---|---|---|
| 77 | O | CH(CH₃)CH(OH)CH₃ | isobutyryl-N,N-diethylamide |
| 78 | O | CH(CH₃)CH(OH)CH₃ | isobutyryl-aziridine |
| 79 | O | CH(CH₃)CH(OH)CH₃ | isobutyryl-azetidine |
| 80 | O | CH(CH₃)CH(OH)CH₃ | isobutyryl-pyrrolidine |
| 81 | O | CH(CH₃)CH(OH)CH₃ | isobutyryl-piperidine |
| 82 | O | CH(CH₃)CH(OH)CH₃ | isobutyryl-morpholine |
| 83 | O | CH(CH₃)CH(OH)CH₃ | isobutyryl-thiomorpholine |
| 84 | O | CH(CH₃)CH(OH)CH₃ | isobutyryl-(1,1-dioxo-thian-4-yl) |
| 85 | O | CH(CH₃)CH(OH)CH₃ | isobutyryl-piperazine |
| 86 | O | CH(CH₃)CH(OH)CH₃ | isobutyryl-(4-methylpiperazine) |

TABLE II-continued

| Example | W | R₄ | R₃ |
|---|---|---|---|
| 87 | O | CH(CH₃)CH(OH)— (R) | piperazine-N-isopropyl, N'-isobutyryl |
| 88 | O | CH(CH₃)CH(OH)— (R) | cinnamyl (CH₂CH=CHPh) |
| 89 | O | CH(CH₃)CH(OH)— (R) | 3-hydroxypropyl branched (CH₂CH₂CH(CH₃)OH-type) |
| 90 | O | CH(CH₃)CH(OH)— (R) | —CH₂CH(CH₃)CH₂OC(O)NH₂ |
| 91 | O | CH(CH₃)CH(OH)— (R) | —CH₂CH(CH₃)CH₂OC(O)-morpholinyl |
| 92 | O | CH(CH₃)CH(OH)— (R) | —CH₂CH(CH₃)CH₂OC(O)-piperidinyl |
| 93 | O | CH(CH₃)CH(OH)— (R) | —CH₂CH(CH₃)CH₂OC(O)-(4-methylpiperazinyl) |
| 94 | absent | —CH(CH₃)CH(O-allyl)— | H |
| 95 | O | —CH(CH₃)CH(O-allyl)— | H |
| 96 | O | —CH(CH₃)CH(O-allyl)— | Ac |
| 97 | O | —CH(CH₃)CH(O-allyl)— | allyl |

TABLE II-continued

| Example | W | R₄ | R₃ |
|---|---|---|---|
| 98 | O | (S)-1-(allyloxy)ethyl | -C(CH₃)₂-C(O)NH₂ |
| 99 | O | (S)-1-(allyloxy)ethyl | -C(CH₃)₂-C(O)N(CH₃)₂ |
| 100 | O | (S)-1-(allyloxy)ethyl | -C(CH₃)₂-C(O)N(CH₂CH₃)₂ |
| 101 | O | (S)-1-(allyloxy)ethyl | -C(CH₃)₂-C(O)-aziridin-1-yl |
| 102 | O | (S)-1-(allyloxy)ethyl | -C(CH₃)₂-C(O)-azetidin-1-yl |
| 103 | O | (S)-1-(allyloxy)ethyl | -C(CH₃)₂-C(O)-pyrrolidin-1-yl |
| 104 | O | (S)-1-(allyloxy)ethyl | -C(CH₃)₂-C(O)-piperidin-1-yl |
| 105 | O | (S)-1-(allyloxy)ethyl | -C(CH₃)₂-C(O)-morpholin-4-yl |
| 106 | O | (S)-1-(allyloxy)ethyl | -C(CH₃)₂-C(O)-thiomorpholin-4-yl |
| 107 | O | (S)-1-(allyloxy)ethyl | -C(CH₃)₂-C(O)-(1,1-dioxo-thiomorpholin-4-yl) |

TABLE II-continued

| Example | W | R₄ | R₃ |
|---|---|---|---|
| 108 | O | (S)-1-methyl-2-(allyloxy)ethyl | piperazine-1-carbonyl (NH) |
| 109 | O | (S)-1-methyl-2-(allyloxy)ethyl | 4-methylpiperazine-1-carbonyl |
| 110 | O | (S)-1-methyl-2-(allyloxy)ethyl | 4-isopropylpiperazine-1-carbonyl |
| 111 | O | (S)-1-methyl-2-(allyloxy)ethyl | (E)-styryl-CH₂- |
| 112 | O | (S)-1-methyl-2-(allyloxy)ethyl | -CH₂CH₂OH |
| 113 | O | (S)-1-methyl-2-(allyloxy)ethyl | -CH₂CH₂OC(O)NH₂ |
| 114 | O | (S)-1-methyl-2-(allyloxy)ethyl | -CH₂CH₂OC(O)-morpholine |
| 115 | O | (S)-1-methyl-2-(allyloxy)ethyl | -CH₂CH₂OC(O)-piperidine |
| 116 | O | (S)-1-methyl-2-(allyloxy)ethyl | -CH₂CH₂OC(O)-(4-methylpiperazine) |
| 117 | absent | (S)-1-methyl-2-(4-hydroxybutoxy)ethyl | H |

TABLE II-continued

| Example | W | R$_4$ | R$_3$ |
|---|---|---|---|
| 118 | O | -O-(CH$_2$)$_4$-OH | H |
| 119 | O | -O-(CH$_2$)$_4$-OH | Ac |
| 120 | O | -O-(CH$_2$)$_4$-OH | allyl |
| 121 | O | -O-(CH$_2$)$_4$-OH | -C(=O)-C(CH$_3$)$_2$-NH$_2$ (isobutyramide) |
| 122 | O | -O-(CH$_2$)$_4$-OH | -C(=O)-N(CH$_3$)$_2$ (dimethylamide, isopropyl) |
| 123 | O | -O-(CH$_2$)$_4$-OH | -C(=O)-N(Et)$_2$ (diethylamide, isopropyl) |
| 124 | O | -O-(CH$_2$)$_4$-OH | aziridinyl carbonyl |
| 125 | O | -O-(CH$_2$)$_4$-OH | azetidinyl carbonyl |
| 126 | O | -O-(CH$_2$)$_4$-OH | pyrrolidinyl carbonyl |
| 127 | O | -O-(CH$_2$)$_4$-OH | piperidinyl carbonyl |
| 128 | O | -O-(CH$_2$)$_4$-OH | morpholinyl carbonyl |

TABLE II-continued

| Example | W | R₄ | R₃ |
|---|---|---|---|
| 129 | O | (S)-CH(CH₃)-O-(CH₂)₄-OH | thiomorpholine-N-C(=O)-CH(CH₃)- |
| 130 | O | (S)-CH(CH₃)-O-(CH₂)₄-OH | 1,1-dioxo-tetrahydrothiopyran-4-yl-C(=O)-CH(CH₃)- |
| 131 | O | (S)-CH(CH₃)-O-(CH₂)₄-OH | piperazine-N-C(=O)-CH(CH₃)- |
| 132 | O | (S)-CH(CH₃)-O-(CH₂)₄-OH | 4-methylpiperazine-N-C(=O)-CH(CH₃)- |
| 133 | O | (S)-CH(CH₃)-O-(CH₂)₄-OH | 4-isopropylpiperazine-N-C(=O)-CH(CH₃)- |
| 134 | O | (S)-CH(CH₃)-O-(CH₂)₄-OH | PhCH=CH-CH₂-CH(CH₃)- |
| 135 | O | (S)-CH(CH₃)-O-(CH₂)₄-OH | HO-CH₂-CH₂-CH(CH₃)- |
| 136 | O | (S)-CH(CH₃)-O-(CH₂)₄-OH | H₂N-C(=O)-O-CH₂-CH₂-CH(CH₃)- |
| 137 | O | (S)-CH(CH₃)-O-(CH₂)₄-OH | morpholine-N-C(=O)-O-CH₂-CH₂-CH(CH₃)- |
| 138 | O | (S)-CH(CH₃)-O-(CH₂)₄-OH | piperidine-N-C(=O)-O-CH₂-CH₂-CH(CH₃)- |

TABLE II-continued
| Example | W | R4 | R3 |
|---|---|---|---|
| 139 | O | 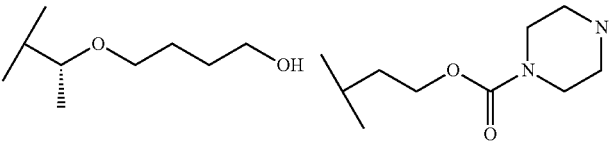 |  |
| 140 | absent | 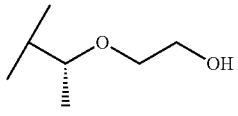 | H |
| 141 | O | 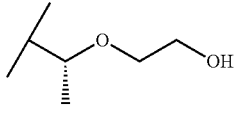 | H |
| 142 | O | 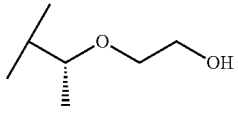 | Ac |
| 143 | O | 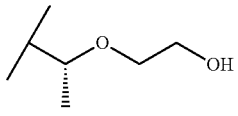 | allyl |
| 144 | O | 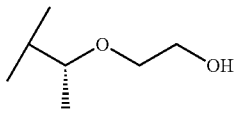 | 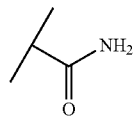 |
| 145 | O | 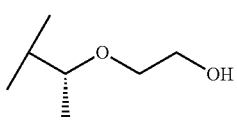 | 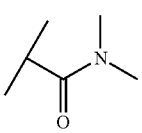 |
| 146 | O | 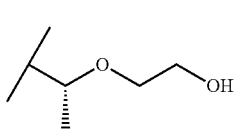 | 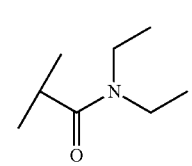 |
| 147 | O | 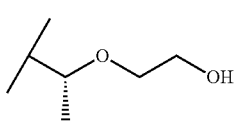 | 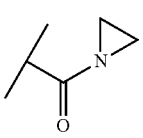 |
| 148 | O | 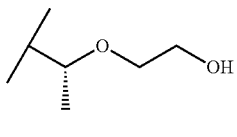 | 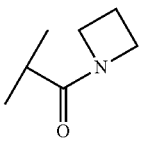 |
| 149 | O | 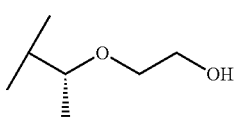 | 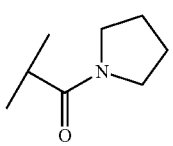 |

TABLE II-continued

| Example | W | R₄ | R₃ |
|---|---|---|---|
| 150 | O | CH(CH₃)-O-CH₂CH₂-OH | C(CH₃)-C(=O)-N(piperidine) |
| 151 | O | CH(CH₃)-O-CH₂CH₂-OH | C(CH₃)-C(=O)-N(morpholine) |
| 152 | O | CH(CH₃)-O-CH₂CH₂-OH | C(CH₃)-C(=O)-N(thiomorpholine) |
| 153 | O | CH(CH₃)-O-CH₂CH₂-OH | C(CH₃)-C(=O)-N(thiomorpholine-S,S-dioxide) |
| 154 | O | CH(CH₃)-O-CH₂CH₂-OH | C(CH₃)-C(=O)-N(piperazine)-NH |
| 155 | O | CH(CH₃)-O-CH₂CH₂-OH | C(CH₃)-C(=O)-N(4-methylpiperazine) |
| 156 | O | CH(CH₃)-O-CH₂CH₂-OH | C(CH₃)-C(=O)-N(4-isopropylpiperazine) |
| 157 | O | CH(CH₃)-O-CH₂CH₂-OH | C(CH₃)-CH=CH-phenyl |
| 158 | O | CH(CH₃)-O-CH₂CH₂-OH | C(CH₃)-CH₂CH₂-OH |
| 159 | O | CH(CH₃)-O-CH₂CH₂-OH | C(CH₃)-CH₂-O-C(=O)-NH₂ |

TABLE II-continued

| Example | W | R₄ | R₃ |
|---|---|---|---|
| 160 | O | (S)-CH(CH₃)-O-CH₂CH₂-OH | -CH₂CH(CH₃)CH₂-O-C(O)-N(morpholinyl) |
| 161 | O | (S)-CH(CH₃)-O-CH₂CH₂-OH | -CH₂CH(CH₃)CH₂-O-C(O)-N(piperidinyl) |
| 162 | O | (S)-CH(CH₃)-O-CH₂CH₂-OH | -CH₂CH(CH₃)CH₂-O-C(O)-N(4-methylpiperazinyl) |
| 163 | absent | (S)-CH(CH₃)-O-CH₂CH₂-N(morpholinyl) | H |
| 164 | O | (S)-CH(CH₃)-O-CH₂CH₂-N(morpholinyl) | H |
| 165 | O | (S)-CH(CH₃)-O-CH₂CH₂-N(morpholinyl) | Ac |
| 166 | O | (S)-CH(CH₃)-O-CH₂CH₂-N(morpholinyl) | allyl |
| 167 | O | (S)-CH(CH₃)-O-CH₂CH₂-N(morpholinyl) | -C(CH₃)₂-C(O)-NH₂ |
| 168 | O | (S)-CH(CH₃)-O-CH₂CH₂-N(morpholinyl) | -C(CH₃)₂-C(O)-N(CH₃)₂ |
| 169 | O | (S)-CH(CH₃)-O-CH₂CH₂-N(morpholinyl) | -C(CH₃)₂-C(O)-N(CH₂CH₃)₂ |

TABLE II-continued
| Example | W | R₄ | R₃ |
|---|---|---|---|
| 170 | O | 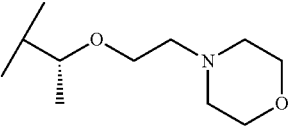 | 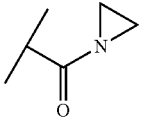 |
| 171 | O | 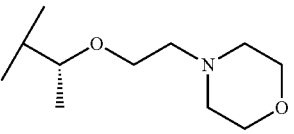 | 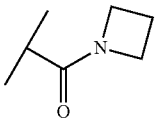 |
| 172 | O | 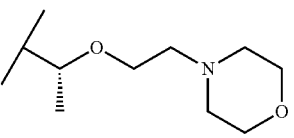 | 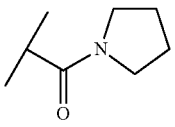 |
| 173 | O | 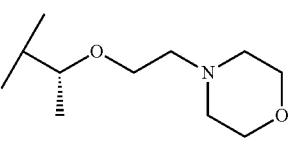 | 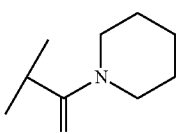 |
| 174 | O | 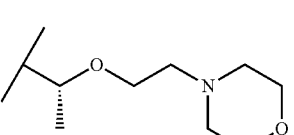 | 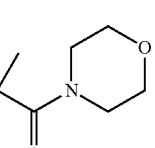 |
| 175 | O | 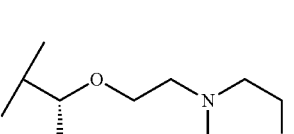 | 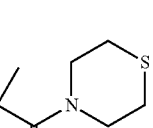 |
| 176 | O | 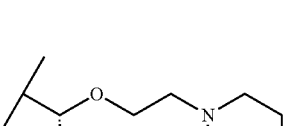 | 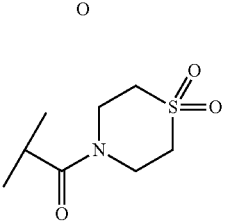 |
| 177 | O | 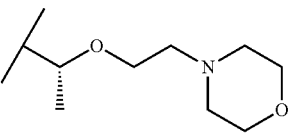 | 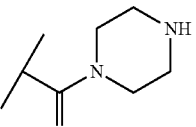 |
| 178 | O | 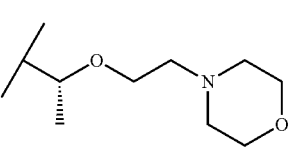 | 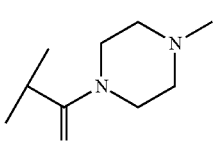 |

TABLE II-continued

| Example | W | R₄ | R₃ |
|---------|---|----|----|
| 179 | O | (2-morpholinoethoxy group) | N-isopropylpiperazine carbonyl |
| 180 | O | (2-morpholinoethoxy group) | cinnamyl |
| 181 | O | (2-morpholinoethoxy group) | hydroxypropyl |
| 182 | O | (2-morpholinoethoxy group) | carbamate (OC(O)NH₂) |
| 183 | O | (2-morpholinoethoxy group) | morpholine carbamate |
| 184 | O | (2-morpholinoethoxy group) | piperidine carbamate |
| 185 | O | (2-morpholinoethoxy group) | 4-methylpiperazine carbamate |

A further embodiment of the present invention includes pharmaceutical compositions comprising any single compound delineated herein, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

As immunosuppressants, the compounds of the present invention are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia greata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' ophthalmopathy, Vogt-Koyanagi-Harada syndrome, sarcoidosis, multiple myeloma, etc.; obstructive airway diseases, which includes conditions such as chronic obstructive pulmonary disease (COPD), asthma (for example, bronchial asthma, allergic asthma, intrinsic asthma, extrinsic asthma and dust asthma), particularly chronic or inveterate asthma (for example, late asthma and airway hyperresponsiveness), bronchitis, allergic rhinitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include, but are not limited to, ischemic bowel diseases, inflammatory bowel diseases, necrotizing enterocolitis, intestinal lesions associated with thermal burns and leukotriene B4-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia reperfusion injury of organs (such as heart, liver, kidney and digestive tract) which occurs upon preservation, transplantation or ischemic disease (for example, thrombosis and cardiac infraction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on.

Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on chronic" liver failure (acute liver failure on chronic liver diseases), and moreover are useful for various diseases because of their useful activity such as augmention of chemotherapeutic effect, preventing or treating activity of cytomegalovirus infection, particularly human cytomegalovirus (HCMV) infection, anti-inflammatory activity, and so on.

The compounds of the present invention may be used as vaccines to treat immunosuppression in a subject. It is sometimes found that the antigen introduced into the body for the acquisition of immunity from disease also acts as an immunosuppressive agent, and therefore, antibodies are not produced by the body and immunity is not acquired. By introducing a compound of the present invention into the body as a vaccine, the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs by inhibiting P-glycoprotein, as they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins (hsp), hsp56 or hsp59, belong to the class of immunophilin proteins (see "HSP70 induction by cyclosporin A in cultured rat hepatocytes: effect of vitamin E succinate," Andres, David et al., *Instituto de Bioqimica, Facultad de Farmacia, Universidad Complutense, Madrid, Spain*. J. Hepatol. (2000) 33(4), 570-579; "Cyclosporin A Induces an Atypical Heat Shock Response," Paslaru, Liliana, et al., Biochem. Biophys. Res. Commun. (2000), 269(2), 464-469; "The cyclosporine A-binding immunophilin CyP-40 and the FK506-binding immunophilin hsp56 bind to a common site on hsp90 and exist in independent cytosolic heterocomplexes with the untransformed glucocorticoid receptor," Owens-Grillo, Janet K. et al., Med. Sch., Univ. Michigan, Ann Arbor, Mich. USA. J. Biol. Chem. (1995), 270(35), 20479-84). The ability of a steroid receptor 10 associated heat shock protein to bind the immunosuppressive CsA suggests that the steroid receptor and immunophilin signal transduction pathways are functionally interrelated.

The combined treatment of compounds of the present invention and low concentrations of a steroid ligand (for e.g., progesterone, dexamethasone) result in a significant enhancement of target gene expression over that seen in response to ligand alone. Thus, the compounds of the present invention potentiate steroidmediated transactivation. Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, scleritis and Graves' ophthalmopathy) and rejection of corneal transplantation.

Accordingly, the pharmaceutical compositions of the present invention comprise a therapeutically effective amount of a cyclosporin analog of the invention (e.g. those of the formulae delineated herein) in combination with a pharmaceutically acceptable carrier or excipient. In particular, compositions pertaining to the present invention are useful for treating a subject for immune-mediated organ or tissue allograft rejection, a graft-versus-host disease, an autoimmune disease, an obstructive airway disease, a hyperproliferative disease, or an ischemic or inflammatory intestinal or bowel disease.

The present invention also relates to method(s) of treatment of immune disorders and inflammation or prevention of organ transplant rejection in a subject by administering to the subject therapeutically effective amounts of the cyclosporin analogs of the present invention with or without the concurrent use of other drugs or pharmaceutically acceptable excipients, as described throughout the present specification.

Yet a further embodiment of the present invention is a pharmaceutical composition comprising any single compound delineated herein in combination with one or more HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to, prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function.

Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121(A2), or U.S. Pat. No. 6,348,587B1 or WO 01/60315 or WO 01/32153 or non-nucleoside inhibitors such as, for example, benzimidazole polymerase inhibitors described in EP1 162196A1 or WO 02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_8$ alkyl," or "$C_1$-$C_{12}$ alkyl," as used herein, refer to saturated, straight- or branched-chain hydrocarbon radicals containing between one and eight, or one and twelve carbon atoms, respectively. Examples of $C_1$-$C_8$ alkyl radicals include, but are not limited to, methyl, ethyl, propyl, isopropyl, n-butyl, tent-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_8$ alkenyl," as used herein, refer to straight- or branched-chain hydrocarbon radicals containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The term "$C_2$-$C_8$ alkynyl," as used herein, refer to straight- or branched-chain hydrocarbon radicals containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but are not limited to, cyclopropyl, cyclobutyl, cyclopentyl, cyclohexyl, cycloheptyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$ cycloalkenyl" or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group. Any cycloalkyl group can also be an alicyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —NO$_2$, —CN, —N$_3$, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —$C(NH)NH$—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)$CH_3$), benzoyl (Bz or —C(O)$C_6H_5$), and trimethylsilyl (TMS or —$Si(CH_3)_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs", Textbook of Drug Design and Development, Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
$Boc_2O$ for di-tert-butyl-dicarbonate;
Boc for t-butoxycarbonyl;
Bz for benzoyl;
Bn for benzyl;
BocNHOH for tent-butyl N-hydroxycarbamate;
t-BuOK for potassium tert-butoxide;
BOP for (benzotriazol-1-yloxy)tris(dimethylamino)phosphonium;
Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
$Et_2O$ for diethyl ether;

HATU for O-(7-azabenzotriazol-1-yl)-N,N,N',N',-tetramethyluronium;
Hexafluorophosphate;
HCl for hydrogen chloride;
HOBT for 1-hydroxybenzotriazole;
$K_2CO_3$ for potassium carbonate;
MeOH for methanol;
Ms for mesyl or $-SO_2-CH_3$;
$Ms_2O$ for methanesulfonic anhydride or mesyl-anhydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
NMMO for N-methylmorpholine N-oxide;
$NaIO_4$ for sodium periodate;
OH for hydroxy;
$OsO_4$ for osmium tetroxide;
TEA or $Et_3N$ for triethylamine;
TFA for trifluoroacetic acid;
THF for tetrahydrofuran;
TPP or $PPh_3$ for triphenylphosphine;
Ts for tosyl or $-SO_2-C_6H_4CH_3$;
$Ts_2O$ for tolylsulfonic anhydride or tosyl-anhydride;
TsOH for p-tolylsulfonic acid;
Pd for palladium;
Ph for phenyl;
$Pd_2(dba)_3$ for tris(dibenzylideneacetone)dipalladium(0);
$Pd(PPh_3)_4$ for tetrakis(triphenylphosphine)palladium(0);
TBS for tent-butyl dimethylsilyl; or
TMS for trimethylsilyl;
TMSCl for trimethylsilyl chloride;
CsA for cyclosporinA.

Synthetic Methods

The compounds and processes of the present invention will be better understood in connection with the following synthetic schemes that illustrate the methods by which the compounds of the invention may be prepared.

The novel cyclosporine analogues of the present invention are derived from cyclosporine A. As shown in Scheme 1, a key intermediate of formula (1-3) was prepared by selective removal of amino acid in position four—N-methyl leucine of cyclosporinA (see Roland Wenger et al, "Synthetic routes to NEtXaa[4]-cyclosporin A derivatives as potential anti-HIV I drugs", *Tetrahedron Letters*, 2000, 41, 7193, which is hereby incorporated by reference in its entirety). Thus, cyclosporinA was reacted with acetic anhydride, optionally in the presence of pyridine or DMAP in $CH_2Cl_2$ to give acetylated intermediate (1-1), which was followed by selective cleavage of the amide bond between position three and position four amino acid with trimethyloxonium tetrafluoroborate in $CH_2Cl_2$ to afford the intermediate (1-2). Edman degradation of (1-2) gave the key intermediate (1-3).

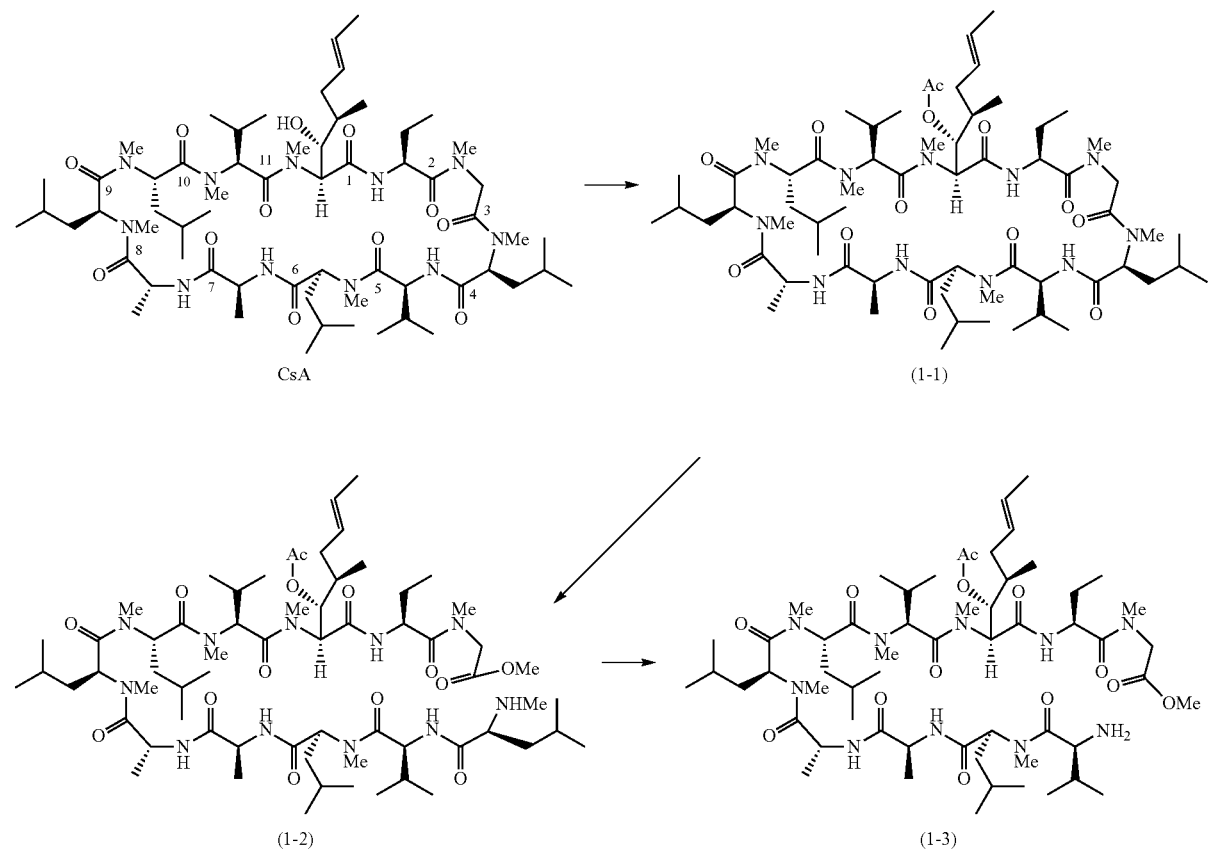

Scheme 1

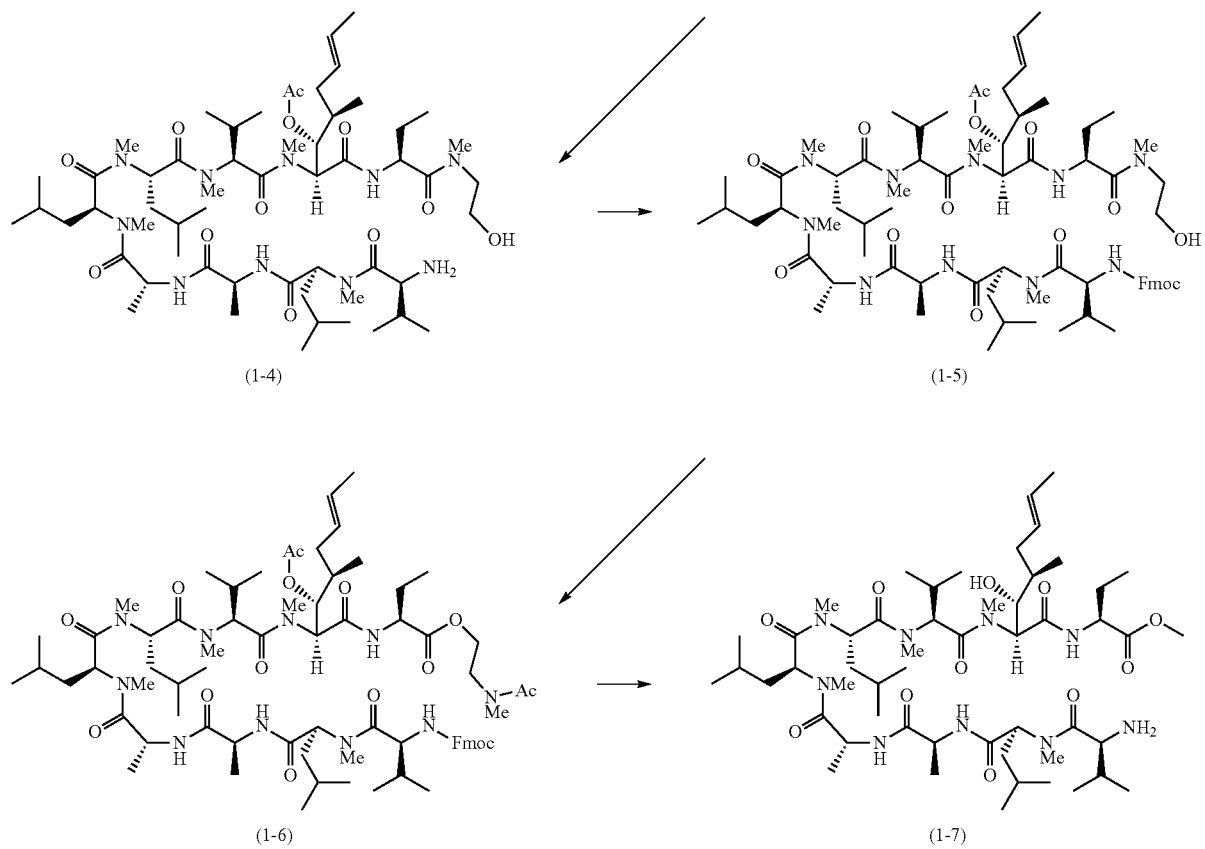

(1-4)

(1-5)

(1-6)

(1-7)

Reduction of the compound of formula (1-3) with reducing agent such as, but not limited to NaBH$_4$ affords the compound of formula (1-4). The reaction is carried out in a protic solvent such as, but not limited to, methanol, ethanol, isopropanol and tert-butanol or the mixture of two protic solvents. The reaction temperature can vary from 0° C. to about 50° C. Protection of the amino group of the compound of formula (1-4) with Fmoc-Cl in the presence of organic base such as, but not limited to, triethylamine, diisopropylethylamine, DBU, N-methylmorpholine and DMAP gives the compound of formula (1-5). The reaction is carried out in an aprotic solvent such as, but not limited to, CH$_2$Cl$_2$, DMF and THF. The reaction temperature can vary from 0° C. to about 50° C. Further rearrangement of the compound of formula (1-5) in the presence of an acid, followed by acetyl protection gives the compound of formula (1-6). Suitable acids include, but are not limited to, methanesulfonic acid, toluenesulfonic acid, camphorsulfonic acid. The rearrangement reaction is carried out in a protic solvent such as, but not limited to, methanol, ethanol, isopropanol and tert-butanol. The acetyl protection reaction is carried out in an aprotic solvent such as, but not limited to, CH$_2$Cl$_2$, ClCH$_2$CH$_2$Cl, DMF and THF with acetic anhydride in the presence of base. The suitable bases include, but are not limited to, triethylamine, diisopropylethylamine, DBU, N-methylmorpholine and DMAP. The compound of formula (1-6) is converted to the compound of formula (1-7) with sodium methoxide in methanol.

Scheme 2 illustrates a process of the invention for the preparation of compounds according to the invention. First the compound of formula (1-2) is coupled with a protected amino acid of the formula (2-1), where W and R$_3$ is as previously defined to give the compound of formula (2-2). The coupling regent can be selected from, but not limited to DCC, EDC, di-isopropyl carbodiimide, BOP—Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, CH$_2$Cl$_2$, DMF and THF. The reaction temperature can vary from 0° C. to about 50° C.

Then the compound of formula (2-2) is converted to the compound of formula (2-3) by NaBH$_4$ reduction in a protic solvent such as, but not limited to, methanol, ethanol, isopropanol and tert-butanol or the mixture of two protic solvents. Further rearrangement of the compound of formula (2-3) in the presence of an acid gives the compound of formula (2-4). Suitable acids include, but are not limited to, methanesulfonic acid, toluenesulfonic acid, camphorsulfonic acid. The rearrangement reaction is carried out in a protic solvent such as, but not limited to, methanol, ethanol, isopropanol and tert-butanol. The Boc group is deprotected under this condition.

Scheme 2
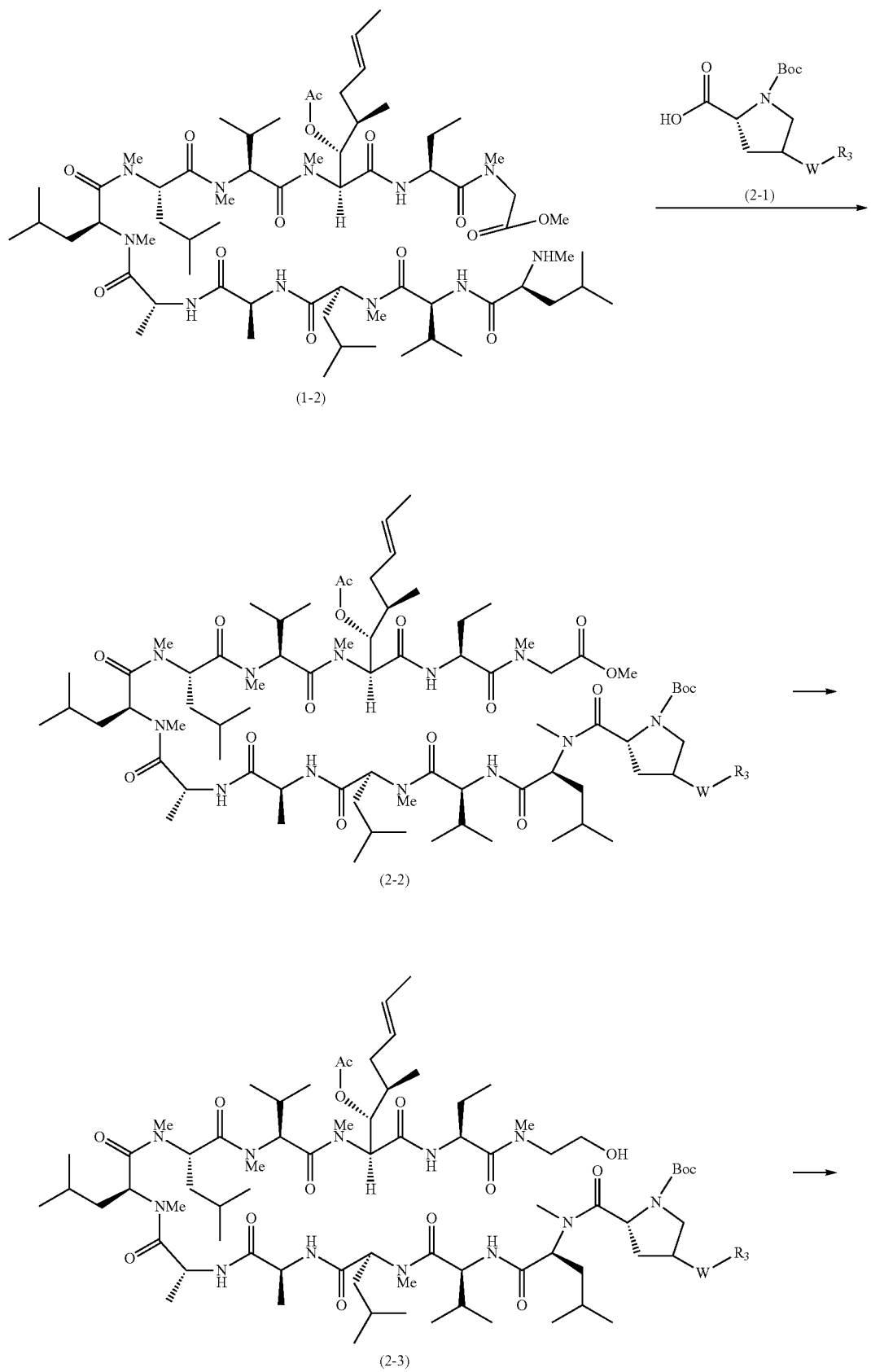

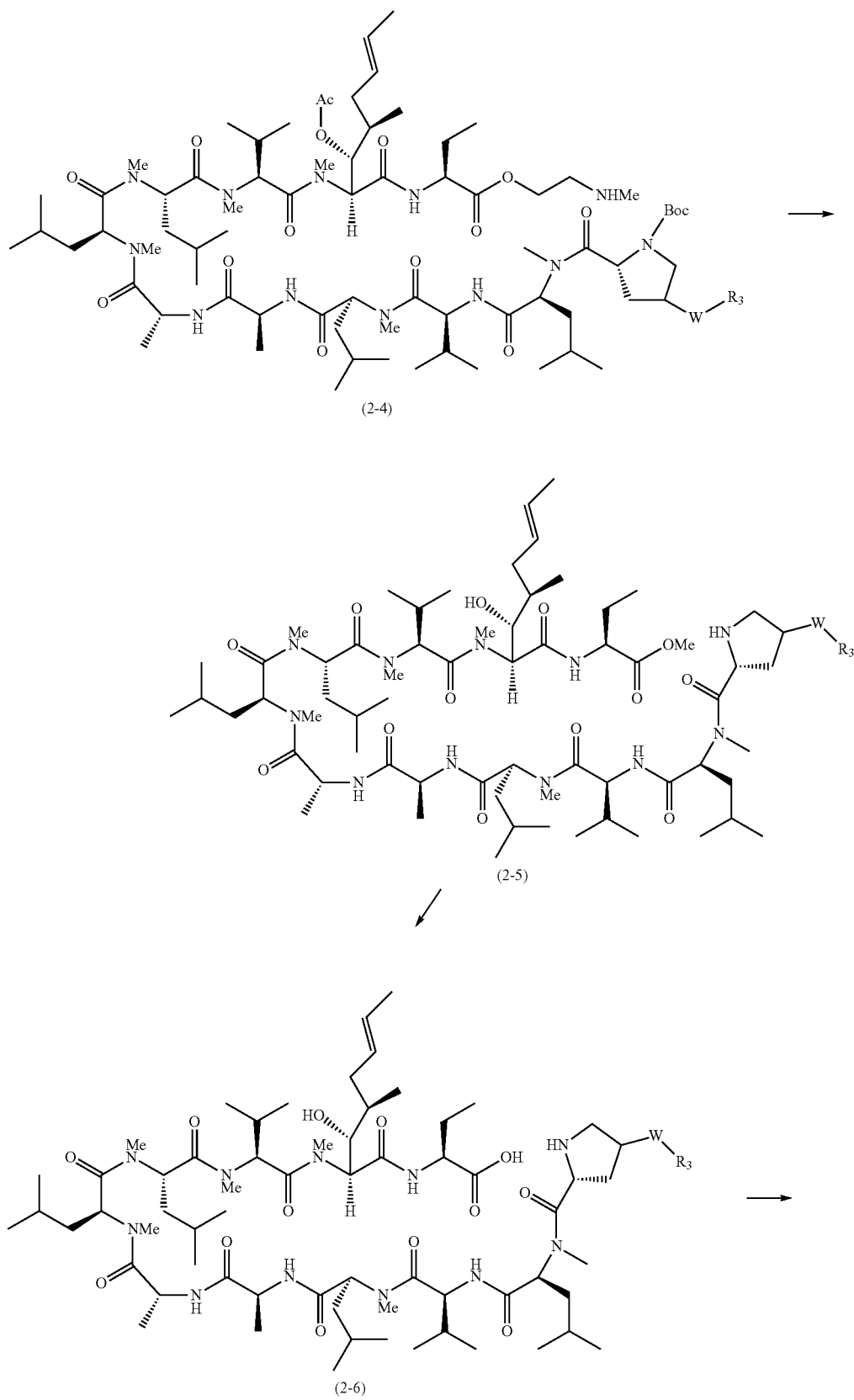

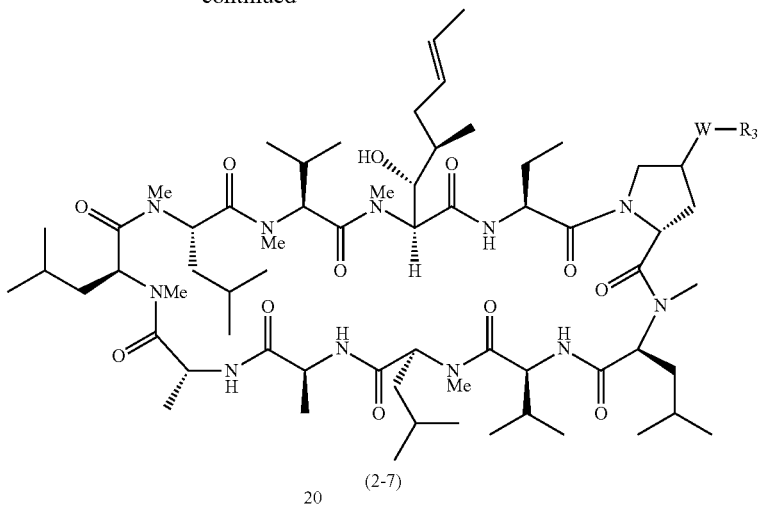

(2-7)

The compound of formula (2-4) is converted to the compound of formula (2-5) with sodium methoxide in methanol. The methyl ester of compound of formula (2-5) is converted to the corresponding acid compound of formula (2-6) via alkaline hydrolysis in protic solvents. Representative alkali compounds include lithium hydroxide, sodium hydroxide, potassium hydroxide, and the like. Suitable solvents include, but are not limited to, methanol, ethanol, isopropanol, butanol, THF, 1,4-dioxane and mixtures thereof. The reaction temperature is preferably 0° to 35° C.

Compound of formula (2-7) is prepared by intramolecular amide formation reaction of the compound of formula (2-6). The reagent can be selected from, but not limited to DCC, EDC, di-isopropyl carbodiimide, BOP—Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

Another alternative process for the preparation of the novel cyclosporin analogues of the present invention is also illustrated in Scheme 3.

First the compound of formula (1-7) is coupled with a protected dipeptide of the formula (3-1), where W, $R_3$ and $R_4$ is as previously defined to give the compound of formula (3-2). The coupling regent can be selected from, but not limited to DCC, EDC, di-isopropyl carbodiimide, BOP—Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

The protected dipeptides of formula (3-1) are prepared by the method described in Hu, T. and Panek, J. S.; *J. Am. Chem. Soc.* 2002, 124, 11372.

The compound of formula (3-2) is converted to the compound of formula (3-3) by acidic Boc deprotection. The acid can be selected from, but not limited to, TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" $3^{rd}$ red., John Wiley & Son, Inc., 1999.

The methyl ester of compound of formula (3-3) is converted to the corresponding acid compound of formula (3-4) via alkaline hydrolysis in protic solvents. Representative alkali compounds include lithium hydroxide, sodium hydroxide, potassium hydroxide, and the like. Suitable solvents include, but are not limited to, methanol, ethanol, isopropanol, butanol, THF, 1,4-dioxane and mixtures there of. The reaction temperature is preferably 0° to 35° C.

Scheme 3

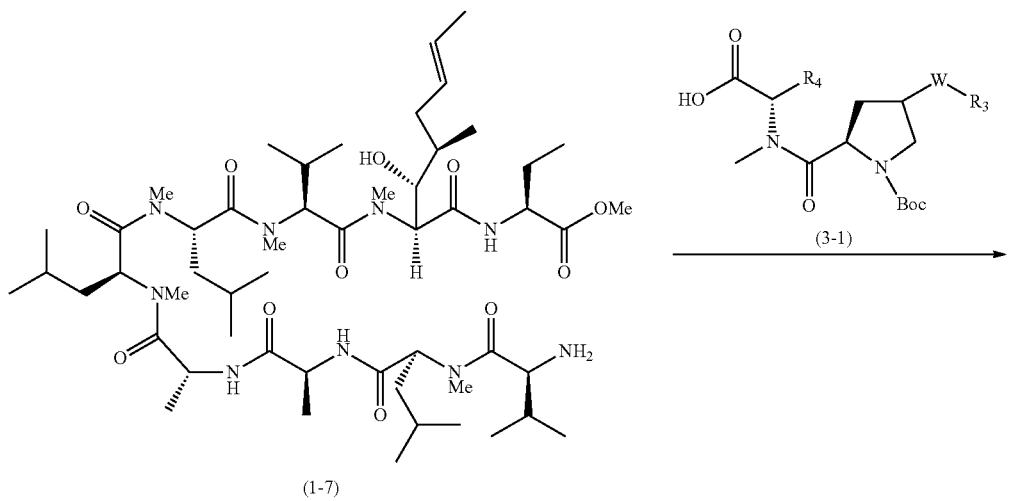

(1-7)  (3-1)

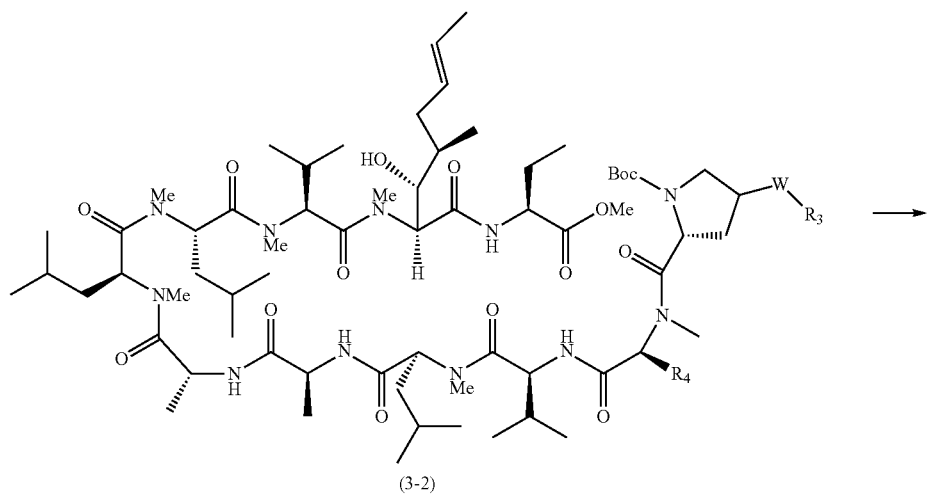
(3-2)
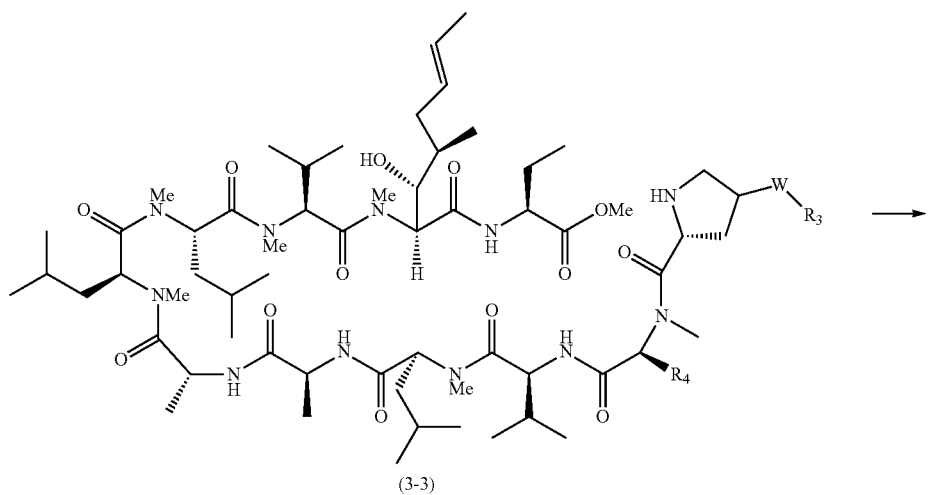
(3-3)
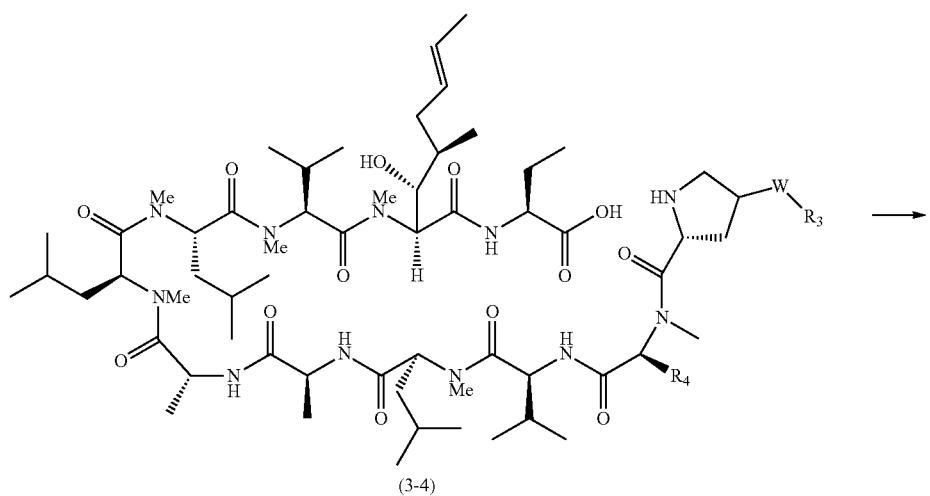
(3-4)

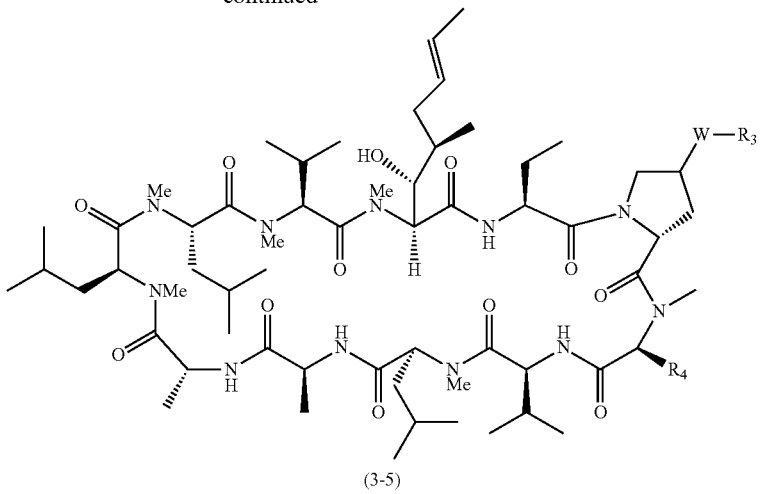

(3-5)

Compound of formula (3-5) is prepared by intramolecular amide formation reaction. The regent can be selected from, but not limited to DCC, EDC, di-isopropyl carbodiimide, BOP—Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

Compound of Formula IV: $R_4$=Isobutyl, W is Absent, and $R_3$=H

Step 1a: Compound of Formula (1-1)

CsA (481 g, 0.4 mol) was dissolved in anhydrous $CH_2Cl_2$ (1.8 L). Acetic anhydride (163.3 g, 1.6 mol) was added followed by DMAP (48.86 g, 0.4 mol) at room temperature under nitrogen. The reaction mixture was stirred for 36 hrs. The reaction mixture was diluted with 6 L of isopropyl acetate, followed by 8 L of water and stirred for 30 mins. The organic layer was separated and washed with saturated $NaHCO_3$ (4×6 L) and brine (6 L). The organic phase was dried over $Na_2SO_4$ and concentrated. The resulted white foam was dried under vacuum to afford the compound of formula (1-1) (520 g, 95.5% HPLC purity).

MS (ESI): 1244.8 m/z (M+1).

Step 1b: Compound of Formula (1-2):

Compound of formula (1-1) (250 g, 0.2 mole) was dissolved in anhydrous $CH_2Cl_2$ (2 L). Trimethyloxoniumtetrafluoroborate (89.12 g, 0.6 mol) was added at 0° C. and the reaction mixture was stirred at room temperature for 20 hrs. Methanol and water (1:1 mixture, 2.5 L) was added via a dropping funnel over 15 mins at 0° C. and then stirred at room temperature for 3 hrs. Reaction mixture was further diluted with 2 L of $CH_2Cl_2$ and 2 L of water. The organic layer was separated and washed with saturated $Na_2CO_3$ (2 L) and brine (2 L), and then dried over $Na_2SO_4$. The solvent was removed and the residue was purified on silica gel column to afford the compound of formula (1-2) (170 g, 92.5% HPLC purity).

MS (ESI): 1276.8 m/z (M+1).

Step 1c: Compound of Formula (1-3):

Compound of formula (1-2) (230 g, 0.18 mole) was dissolved in anhydrous THF (1.5 L) and Phenyl thioisocyanate (24.35 g, 0.18 mole) was added over 15 mins at 0° C. The reaction mixture was stirred at room temperature for 2 hrs and diluted with 1 L of water and 2.5 L of ethyl acetate. The organic layer was separated and washed with brine (1 L), and then dried over $Na_2SO_4$, and concentrated. After dried under vacuum for 24 hrs, the residue was dissolved in anhydrous $CH_2Cl_2$ (2.66 L). TFA (455 mL) was added at 0° C. over 30 mins and the reaction mixture was stirred at room temperature for 4 hours. Reaction was quenched with saturated $Na_2CO_3$ (3 L) at −15° C. The organic layer was separated and washed with brine (3 L), and then dried over $MgSO_4$. Concentrated and the residue was purified on silica gel column to afford the compound of formula (1-3) (130 g).

Step 1d: Compound of Formula (2-2):

To a solution of the compound of formula (1-3) (1.28 g, 1.0 mmol), Boc-D-proline (323 mg, 1.5 mmol) and DMAP (244 mg, 2.0 mmol) in DCM (10 mL) was added HATU (0.76 g, 2 mmol) at 0° C. After stirred at room temperature for 14 hrs, the reaction mixture was quenched with 10% aqueous $Na_2CO_3$ and extracted with DCM. The organic layer was washed with saturated $KHSO_4$ solution, brine and dried over anhydrous $Na_2SO_4$, filtered, concentrated, and purified by flash chromatography (ethyl acetate/MeOH, 100-85%, v/v) to give the compound of formula (2-2) as white foam (1.1 g, 75% yield). ESI MS m/z=1473.84 [M+H]

Step 1e: Compound of Formula (2-3):

To a solution of the compound of formula (2-2) (1.1 g, 0.75 mmol) in methanol (15 mL) was added NaBH$_4$ (500 mg, 10 portion in every 15 min.). After stirred at room temperature for 2 hrs, the reaction mixture was quenched with 10% citric acid (50 ml) at 0° C. Extracted with ethyl acetate (100 ml) and washed with 10% citric acid and brine, dried over anhydrous Na$_2$SO$_4$ and filtered. The solvent was removed and the residue was purified on a silica gel column. (ethyl acetate/MeOH, 100-80%, v/v) to give the compound of formula (2-3) as white foam (1.0 g, 92% yield). ESI MS m/z=1445.88 [M+H]$^+$.

Step 1f: Compound of Formula (2-4):

To a solution of the compound of formula (2-3) (1.0 g, 6.9 mmol) in methanol (20 mL) was added methanesulfonic acid (2 ml). The reaction mixture was stirred at 50° C. for 3 hrs and the solvent was removed. The residue was diluted with ethyl acetate (50 ml) and added saturated Na$_2$CO$_3$ (50 ml). The organic layer was washed with brine and dried over anhydrous Na2SO4. Concentrated and the residue was purified on silica gel column (DCM/MeOH, 100-70%, v/v) to give the compound of formula (2-4) as a white foam (0.8 g, 86% yield). ESI MS m/z=1345.82 [M+H]$^+$.

Step 1g: Compound of Formula (2-6):

To a solution of the compound of formula (2-4) (0.8 g, 0.60 mmol) in methanol (20 mL) was added NaOMe (300 mg) at 0° C. After stirred at room temperature for 8 hrs, NaOH (1N, 10 ml) was added and the mixture was stirred at room temperature for 24 hrs. The reaction was quenched with saturated NaHCO$_3$ (100 ml) and the mixture was extracted with ethyl acetate (100 ml). The organic layer was washed with saturated NaHCO$_3$ and brine. Concentrated to give the compound of formula (2-6) (350 mg, 49%), which was used for next step reaction without further purification.

Step 1h: Compound of Formula (2-7):

To a solution of HATU (152 mg, 0.4 mmol), DMAP (50 mg, 0.4 mmol) in DCM (200 mL) was added a solution of the compound of formula (2-6) (250 mg, 0.2 mmol) in DCM (20 mL) in 2 hrs at room temperature. The solution was stirred at room temperature for 16 hrs, concentrated, quenched with saturated NaHCO$_3$ (100 ml). The organic layer was separated and dried over anhydrous Na$_2$SO$_4$. The solvent was removed and the residue was purified on silica gel column to give the compound formula (2-7) as white foam (185 mg, 75% yield). ESI MS m/z=1228.90 [M+H]$^+$.

Example 2

Compound of Formula IV: R$_4$=Isobutyl, W=O, and R$_3$=H

The compound of example 2 was prepared by using essential same procedure as the preparation of the compound of example 1.

Example 3

Compound of Formula IV: R$_4$=Isobutyl, W=O, and R$_3$=Me

A mixture of the compound of example 2 (25 mg), MeI (0.1 ml) and (t-Bu)$_4$NBr (20 mg) in DCM (1 ml) and 10N NaOH (1 ml) was stirred at room temperature for 48 hrs. The mixture was diluted with DCM (10 ml) and washed with saturated NaHCO3. Dried over anhydrous Na2SO4 and concentrated. The residue was purified on HPLC to give the compound of example 3 (20 mg, 79% yield). ESI MS m/z=1258.74 [M+H]$^+$.

Example 4

Compound of Formula IV: R$_4$=Isobutyl, W=O, and R$_3$=Ac

The compound of example 4 was prepared by using essential same procedure as the preparation of the compound of example 1.

Example 5

Compound of Formula IV: R$_4$=Isobutyl, W=O, and R$_3$=allyl

The compound of example 5 was prepared by using essential same procedure as the preparation of the compound of example 3.

Example 6

Compound of Formula IV: R$_4$=Isobutyl, W=O, and R$_3$=—C(O)NH$_2$

To a solution of the compound of example 2 (25 mg, 0.02 mmol) and triethyl amine (7 ul, 0.05 mmol) was added trichloroacetyl isocyanate (0.05 mmol) at 0° C. The reaction mixture was stirred at 0° C. for 10 min. and was added methanol (15 ml). The mixture was stirred at room temperature for 3 hrs. The solvent was removed and the residued was purified on HPLC to give the compound of example 6 (18 mg, 70% yield). ESI MS m/z=1287.90 [M+H]$^+$.

Example compounds 7-24 of the formula IV, wherein W, R$_4$ and R$_3$ are delineated for each example in Table I are prepared from the compound of example 1 via the method delineated in example 3 and example 6.

TABLE I

| Example | W | R$_4$ | R$_3$ |
|---|---|---|---|
| 7 | O | isobutyl | —C(O)N(CH$_3$)— |
| 8 | O | isobutyl | —C(O)N(Et)$_2$ |
| 9 | O | isobutyl | —C(O)-aziridinyl |
| 10 | O | isobutyl | —C(O)-azetidinyl |

TABLE I-continued

| Example | W | R4 | R3 |
|---|---|---|---|
| 11 | O | isobutyl | pyrrolidinyl carbonyl |
| 12 | O | isobutyl | piperidinyl carbonyl |
| 13 | O | isobutyl | morpholinyl carbonyl |
| 14 | O | isobutyl | thiomorpholinyl carbonyl |
| 15 | O | isobutyl | thiomorpholinyl-1,1-dioxide carbonyl |
| 16 | O | isobutyl | piperazinyl carbonyl |
| 17 | O | isobutyl | 4-methylpiperazinyl carbonyl |
| 18 | O | isobutyl | 4-isopropylpiperazinyl carbonyl |
| 19 | O | isobutyl | cinnamyl |
| 20 | O | isobutyl | 3-hydroxypropyl |
| 21 | O | isobutyl | carbamoyloxypropyl |
| 22 | O | isobutyl | morpholinylcarbonyloxypropyl |
| 23 | O | isobutyl | piperidinylcarbonyloxypropyl |
| 24 | O | isobutyl | 4-methylpiperazinylcarbonyloxypropyl |

Example 25

Compound of Formula IV: R$_4$=Isopropyl, W=Absent, and R$_3$=H

Step 25a: Compound of Formula (1-3):

Compound of formula (1-2) (230 g, 0.18 mole) was dissolved in anhydrous THF (1.5 L) and Phenyl thioisocyanate (24.35 g, 0.18 mole) was added over 15 mins at 0° C. The reaction mixture was stirred at room temperature for 2 hrs and diluted with 1 L of water and 2.5 L of ethyl acetate. The organic layer was separated and washed with brine (1 L), and then dried over Na$_2$SO$_4$, and concentrated. After dried under vacuum for 24 hrs, the residue was dissolved in anhydrous CH$_2$Cl$_2$ (2.66 L). TFA (455 mL) was added at 0° C. over 30 mins and the reaction mixture was stirred at room temperature for 4 hours. Reaction was quenched with saturated Na$_2$CO$_3$ (3 L) at −15° C. The organic layer was separated and washed with brine (3 L), and then dried over MgSO$_4$. Concentrated and the residue was purified on silica gel column to afford the compound of formula (1-3) (130 g).

Step 25b: Compound of Formula (1-4):

Compound of formula (1-3) (61 g, 53 mmole) was dissolved in isopropanol (450 ml) and methanol (50 ml), and NaBH4 (9.0 g, 266 mmole) was added during 1 hrs 1 at 0° C. The reaction mixture was stirred at room temperature for 2 hrs. Ethyl acetate (50 ml) was added and the mixture was stirred at room temperature for 30 min and then quenched with 1N HCl at 0° C. The pH of mixture was adjusted to pH~9 by adding saturated NaHCO$_3$ and Na$_2$CO$_3$. Extracted with ethyl acetate and washed with saturated NaHCO$_3$ and brine. Dried over Na$_2$SO$_4$ and the solvent was removed. The residue was dried on vacuum to give the compound of formula (1-4) (59.7 g)

Step 25c: Compound of Formula (1-5):

Compound of formula (1-4) (22.4 g, 20 mmole) was dissolved in DCM (200 ml). FmocCl (4.92 g, 19 mmole) and DIPEA (5.17 g, 40 mmol) were added at 0° C. The reaction mixture was stirred at 0° C. for 2 hrs. Diluted with DCM (500 ml) and washed with 10% citric acid, saturated NaHCO$_3$ and brine. Dried over Na$_2$SO$_4$ and the solvent was removed. The residue was purified on by silica gel column to give the compound of formula (1-5) (21 g).

Step 25d: Compound of Formula (1-6):

Compound of formula (1-5) (13.4 g, 10 mmole) was dissolved in isopropanol (100 ml). Methanesulfonic acid (100 mmole) was added at room temperature. The reaction mixture was stirred at 50° C. for 8 hrs. The reaction mixture was condensed to ~40 ml and was diluted with ethyl acetate (500 ml) and quenched with saturated NaHCO$_3$. The pH of the mixture was further adjusted to ~9 by adding saturated Na$_2$CO$_3$. Organic layer was separated and washed with brine. Dried over Na$_2$SO$_4$ and the solvent was removed. The residue was dissolved in DCM (100 ml) and was added acetic anhydride (2.04 g, 20 mmol) followed by TEA (4.04 g, 40 mmol). The mixture was stirred at room temperature for 3 hrs and quenched with saturated NaHCO3. The organic layer was separated and washed with brine. Dried over Na$_2$SO$_4$ and concentrated. The residue was purified on a silica gel column to give the compound of formula (1-6) (10 g).

Step 25e: Compound of Formula (1-7):

Compound of formula (1-6) (6.9 g, 5 mmole) was dissolved in methanol (50 ml). NaOMe (2N in methanol, 25 ml) was added at room temperature. The reaction mixture was stirred at room temperature for 18 hrs and quenched with saturated NaHCO$_3$. The pH of the mixture was further adjusted to ~9 by adding saturated Na$_2$CO$_3$. Organic layer was separated and washed with brine. Dried over Na$_2$SO$_4$ and the solvent was removed. The residue was purified on by silica gel column to give the compound of formula (1-7) (4.2 g).

Step 25f: Compound of Formula (3-2):

To a solution of the compound of formula (1-7) (1.04 g, 1.0 mmol), the compound of formula (3-1), where R$_4$ is isopropyl, W is absent and R$_3$ is H (492 mg, 1.5 mmol) and DMAP (244 mg, 2.0 mmol) in DCM (20 mL) was added HATU (0.76 g, 2 mmol) at 0° C. After stirred at room temperature for 14 hrs, the reaction mixture was quenched with 10% aqueous Na$_2$CO$_3$ and extracted with DCM. The organic layer was washed with saturated KHSO$_4$ solution, brine and dried over anhydrous Na$_2$SO$_4$, filtered, concentrated, and purified by flash chromatography (ethyl acetate/MeOH, 100-85%, v/v) to give the compound of formula (3-2) as white foam (1.15 g, 85% yield). ESI MS m/z=1346.64 [M+H]$^+$.

Step 25g: Compound of Formula (3-3):

A solution of the compound of formula (3-2) (1.08 g, 0.8 mmol) in DCM (10 ml) and TFA (5 ml) was stirred at room temperature for 2 hrs. Diluted with DCM (100 ml) and quenched with saturated Na2CO3 (100 ml). The organic layer was separated and washed with saturated Na$_2$CO$_3$ (100 ml×2). Dried over anhydrous Na$_2$SO$_4$, filtered, concentrated to give crude compound of formula (3-3) as white foam (0.94 g). ESI MS m/z=1246.74 [M+H]$^+$.

Step 25h: Compound of Formula (3-4):

To a solution of the compound of formula (3-3) (0.87 g, 0.7 mmol) in THF (20 ml) was added aqueous LiOH (0.5 N, 2.8 ml) at 0° C. The mixture was stirred at 0° C. for 3 hrs and quenched with saturated NaHCO$_3$ (50 ml). Extracted with EtOAc (50 ml) and washed with brine (50 ml×2), dried over anhydrous Na$_2$SO$_4$, filtered, concentrated to give crude compound of formula (3-4) as white foam (0.73 g). ESI MS m/z=1232.64 [M+H]$^+$.

Step 25i: Compound of Formula (3-5):

To a solution of HATU (380 mg, 1 mmol), DMAP (122 mg, 1 mmol) in DCM (200 mL) was added a solution of the compound of formula (3-4) (620 mg, 0.5 mmol) in DCM (20 mL) in 2 hrs at room temperature. The solution was stirred at room temperature for 16 hrs, concentrated, quenched with saturated NaHCO$_3$ (100 ml). The organic layer was separated and dried over anhydrous Na$_2$SO$_4$. The solvent was removed and the residue was purified on silica gel column to give the title compound of example 25 as a white foam (480 mg, 80% yield). ESI MS m/z=1214.92 [M+H]$^+$.

Example compounds 26-185 of the formula IV, wherein W, R$_4$ and R$_3$ are delineated for each example in Table II, are prepared using the general method set forth above for example 25.

TABLE II

| Example | W | R$_4$ | R$_3$ |
|---|---|---|---|
| 25 | absent | tert-butyl | H |
| 26 | O | tert-butyl | H |
| 27 | O | tert-butyl | Ac |
| 28 | O | tert-butyl | allyl |

TABLE II-continued

| Example | W | R₄ | R₃ |
|---|---|---|---|
| 29 | O | isopropyl | -CH(CH₃)-C(=O)-NH₂ |
| 30 | O | isopropyl | -CH(CH₃)-C(=O)-N(CH₃)₂ |
| 31 | O | isopropyl | -CH(CH₃)-C(=O)-N(Et)₂ |
| 32 | O | isopropyl | -CH(CH₃)-C(=O)-N(aziridinyl) |
| 33 | O | isopropyl | -CH(CH₃)-C(=O)-N(azetidinyl) |
| 34 | O | isopropyl | -CH(CH₃)-C(=O)-N(pyrrolidinyl) |
| 35 | O | isopropyl | -CH(CH₃)-C(=O)-N(piperidinyl) |
| 36 | O | isopropyl | -CH(CH₃)-C(=O)-N(morpholinyl) |
| 37 | O | isopropyl | -CH(CH₃)-C(=O)-N(thiomorpholinyl) |
| 38 | O | isopropyl | -CH(CH₃)-C(=O)-N(thiomorpholinyl-S,S-dioxide) |

TABLE II-continued
| Example | W | R4 | R3 |
|---|---|---|---|
| 39 | O | 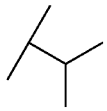 | 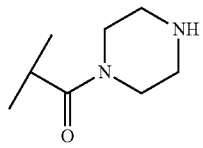 |
| 40 | O | 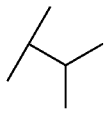 | 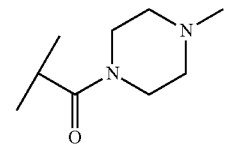 |
| 41 | O | 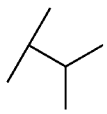 | 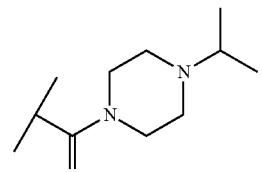 |
| 42 | O | 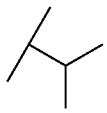 | 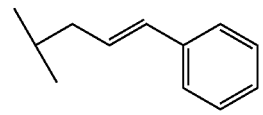 |
| 43 | O | 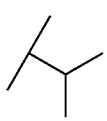 | 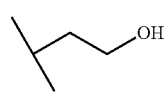 |
| 44 | O | 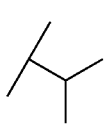 | 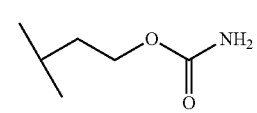 |
| 45 | O | 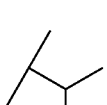 | 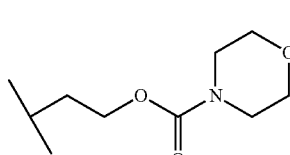 |
| 46 | O | 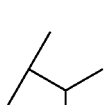 | 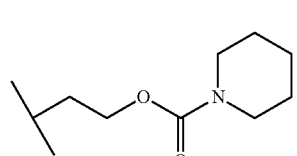 |
| 47 | O | 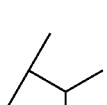 | 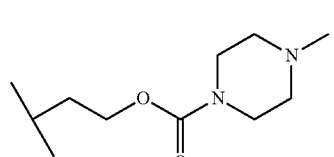 |
| 48 | O | 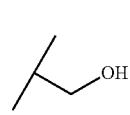 | H |
| 49 | O | 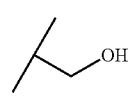 | H |

TABLE II-continued

| Example | W | R₄ | R₃ |
|---|---|---|---|
| 50 | O | CH(CH₃)CH₂OH | Ac |
| 51 | O | CH(CH₃)CH₂OH | allyl |
| 52 | O | CH(CH₃)CH₂OH | –C(CH₃)(C(O)NH₂) |
| 53 | O | CH(CH₃)CH₂OH | –C(CH₃)(C(O)N(CH₃)₂) |
| 54 | O | CH(CH₃)CH₂OH | –C(CH₃)(C(O)N(Et)₂) |
| 55 | O | CH(CH₃)CH₂OH | –C(CH₃)(C(O)-aziridin-1-yl) |
| 56 | O | CH(CH₃)CH₂OH | –C(CH₃)(C(O)-azetidin-1-yl) |
| 57 | O | CH(CH₃)CH₂OH | –C(CH₃)(C(O)-pyrrolidin-1-yl) |
| 58 | O | CH(CH₃)CH₂OH | –C(CH₃)(C(O)-piperidin-1-yl) |
| 59 | O | CH(CH₃)CH₂OH | –C(CH₃)(C(O)-morpholin-4-yl) |
| 60 | O | CH(CH₃)CH₂OH | –C(CH₃)(C(O)-thiomorpholin-4-yl) |

TABLE II-continued

| Example | W | R$_4$ | R$_3$ |
|---|---|---|---|
| 61 | O | isobutanol | 4-(isobutyryl)thiomorpholine 1,1-dioxide |
| 62 | O | isobutanol | 1-(isobutyryl)piperazine |
| 63 | O | isobutanol | 1-(isobutyryl)-4-methylpiperazine |
| 64 | O | isobutanol | 1-(isobutyryl)-4-isopropylpiperazine |
| 65 | O | isobutanol | (E)-4-phenylbut-3-en-1-yl |
| 66 | O | isobutanol | 3-methylbutan-1-ol |
| 67 | O | isobutanol | 3-methylbutyl carbamate |
| 68 | O | isobutanol | 3-methylbutyl morpholine-4-carboxylate |
| 69 | O | isobutanol | 3-methylbutyl piperidine-1-carboxylate |
| 70 | O | isobutanol | 3-methylbutyl 4-methylpiperazine-1-carboxylate |

TABLE II-continued

| Example | W | R₄ | R₃ |
|---|---|---|---|
| 71 | O | CH(CH₃)-CH(OH)-CH₃ (with stereochemistry) | H |
| 72 | O | CH(CH₃)-CH(OH)-CH₃ (with stereochemistry) | H |
| 73 | O | CH(CH₃)-CH(OH)-CH₃ (with stereochemistry) | Ac |
| 74 | O | CH(CH₃)-CH(OH)-CH₃ (with stereochemistry) | allyl |
| 75 | O | CH(CH₃)-CH(OH)-CH₃ (with stereochemistry) | -C(CH₃)₂-C(=O)-NH₂ |
| 76 | O | CH(CH₃)-CH(OH)-CH₃ (with stereochemistry) | -C(CH₃)₂-C(=O)-N(CH₃)₂ |
| 77 | O | CH(CH₃)-CH(OH)-CH₃ (with stereochemistry) | -C(CH₃)₂-C(=O)-N(Et)₂ |
| 78 | O | CH(CH₃)-CH(OH)-CH₃ (with stereochemistry) | -C(CH₃)₂-C(=O)-N(aziridinyl) |
| 79 | O | CH(CH₃)-CH(OH)-CH₃ (with stereochemistry) | -C(CH₃)₂-C(=O)-N(azetidinyl) |
| 80 | O | CH(CH₃)-CH(OH)-CH₃ (with stereochemistry) | -C(CH₃)₂-C(=O)-N(pyrrolidinyl) |
| 81 | O | CH(CH₃)-CH(OH)-CH₃ (with stereochemistry) | -C(CH₃)₂-C(=O)-N(piperidinyl) |

TABLE II-continued

| Example | W | R₄ | R₃ |
|---|---|---|---|
| 82 | O | CH(CH₃)CH(OH)CH₃ | C(CH₃)₂C(O)-morpholine |
| 83 | O | CH(CH₃)CH(OH)CH₃ | C(CH₃)₂C(O)-thiomorpholine |
| 84 | O | CH(CH₃)CH(OH)CH₃ | C(CH₃)₂C(O)-thiomorpholine-1,1-dioxide |
| 85 | O | CH(CH₃)CH(OH)CH₃ | C(CH₃)₂C(O)-piperazine |
| 86 | O | CH(CH₃)CH(OH)CH₃ | C(CH₃)₂C(O)-(4-methyl-piperazine) |
| 87 | O | CH(CH₃)CH(OH)CH₃ | C(CH₃)₂C(O)-(4-isopropyl-piperazine) |
| 88 | O | CH(CH₃)CH(OH)CH₃ | C(CH₃)₂CH=CH-phenyl |
| 89 | O | CH(CH₃)CH(OH)CH₃ | C(CH₃)₂CH₂CH₂OH |
| 90 | O | CH(CH₃)CH(OH)CH₃ | C(CH₃)₂CH₂CH₂OC(O)NH₂ |
| 91 | O | CH(CH₃)CH(OH)CH₃ | C(CH₃)₂CH₂CH₂OC(O)-morpholine |

TABLE II-continued

| Example | W | R₄ | R₃ |
|---|---|---|---|
| 92 | O | CH(CH₃)CH(OH)— (R) | piperidine-1-carboxylate via isopentyl linker |
| 93 | O | CH(CH₃)CH(OH)— (R) | 4-methylpiperazine-1-carboxylate via isopentyl linker |
| 94 | O | CH(CH₃)CH(O-allyl)— | H |
| 95 | O | CH(CH₃)CH(O-allyl)— | H |
| 96 | O | CH(CH₃)CH(O-allyl)— | Ac |
| 97 | O | CH(CH₃)CH(O-allyl)— | allyl |
| 98 | O | CH(CH₃)CH(O-allyl)— | —C(CH₃)₂C(O)NH₂ |
| 99 | O | CH(CH₃)CH(O-allyl)— | —C(CH₃)₂C(O)N(CH₃)₂ |
| 100 | O | CH(CH₃)CH(O-allyl)— | —C(CH₃)₂C(O)N(Et)₂ |
| 101 | O | CH(CH₃)CH(O-allyl)— | —C(CH₃)₂C(O)-aziridin-1-yl |
| 102 | O | CH(CH₃)CH(O-allyl)— | —C(CH₃)₂C(O)-azetidin-1-yl |

TABLE II-continued
| Example | W | R₄ | R₃ |
|---|---|---|---|
| 103 | O | 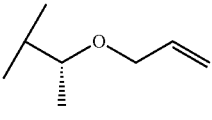 | 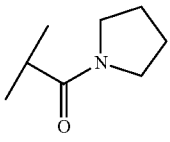 |
| 104 | O | 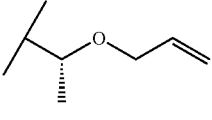 | 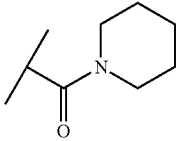 |
| 105 | O | 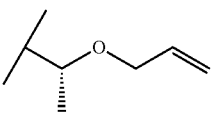 | 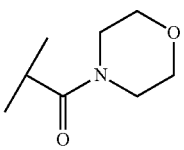 |
| 106 | O | 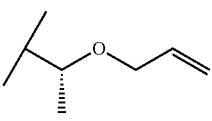 | 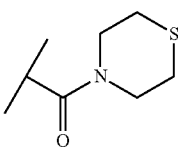 |
| 107 | O | 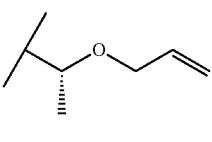 | 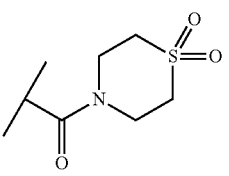 |
| 108 | O | 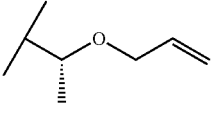 | 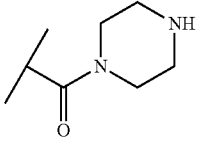 |
| 109 | O | 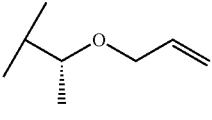 | 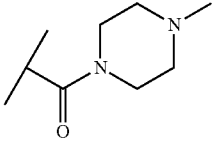 |
| 110 | O | 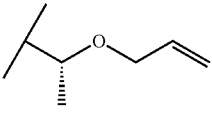 | 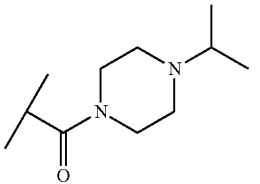 |
| 111 | O | 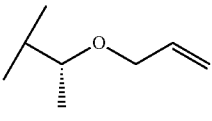 | 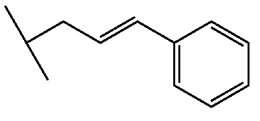 |
| 112 | O | 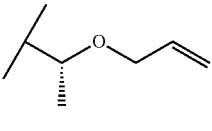 | 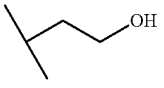 |

TABLE II-continued
| Example | W | R4 | R3 |
|---|---|---|---|
| 113 | O | 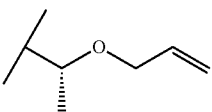 | 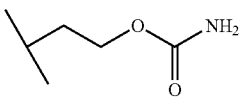 |
| 114 | O | 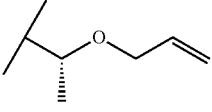 | 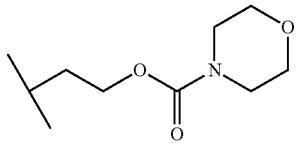 |
| 115 | O | 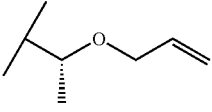 | 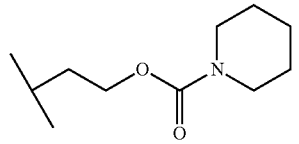 |
| 116 | O | 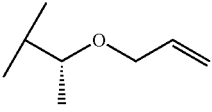 | 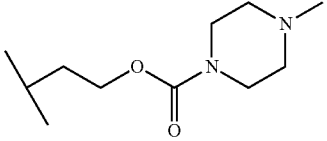 |
| 117 | O | 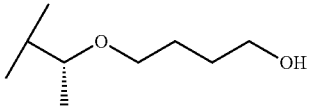 | H |
| 118 | O | 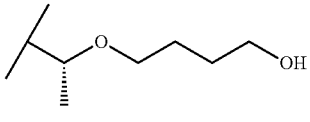 | H |
| 119 | O | 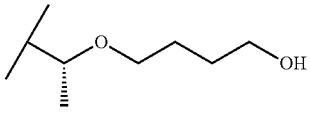 | Ac |
| 120 | O | 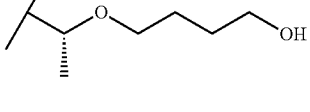 | allyl |
| 121 | O | 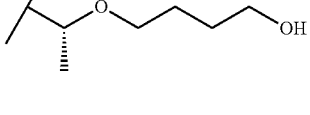 | 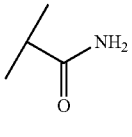 |
| 122 | O | 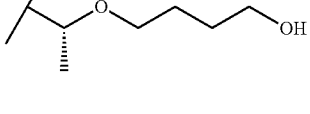 | 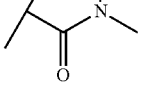 |
| 123 | O | 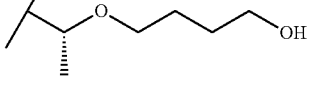 | 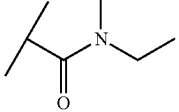 |

TABLE II-continued

| Example | W | R₄ | R₃ |
|---|---|---|---|
| 124 | O | (S)-CH(CH₃)-O-(CH₂)₄-OH | -C(O)-N(aziridine) |
| 125 | O | (S)-CH(CH₃)-O-(CH₂)₄-OH | -C(O)-N(azetidine) |
| 126 | O | (S)-CH(CH₃)-O-(CH₂)₄-OH | -C(O)-N(pyrrolidine) |
| 127 | O | (S)-CH(CH₃)-O-(CH₂)₄-OH | -C(O)-N(piperidine) |
| 128 | O | (S)-CH(CH₃)-O-(CH₂)₄-OH | -C(O)-N(morpholine) |
| 129 | O | (S)-CH(CH₃)-O-(CH₂)₄-OH | -C(O)-N(thiomorpholine) |
| 130 | O | (S)-CH(CH₃)-O-(CH₂)₄-OH | -C(O)-N(thiomorpholine-1,1-dioxide) |
| 131 | O | (S)-CH(CH₃)-O-(CH₂)₄-OH | -C(O)-N(piperazine)-NH |
| 132 | O | (S)-CH(CH₃)-O-(CH₂)₄-OH | -C(O)-N(piperazine)-N-CH₃ |

TABLE II-continued
| Example | W | R₄ | R₃ |
|---|---|---|---|
| 133 | O | 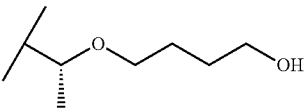 | 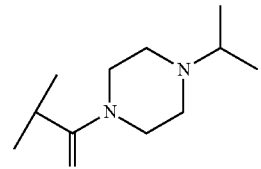 |
| 134 | O | 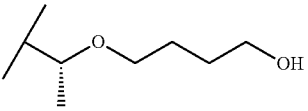 | 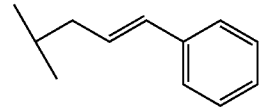 |
| 135 | O | 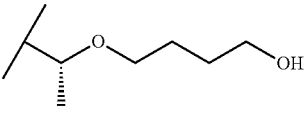 | 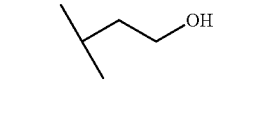 |
| 136 | O | 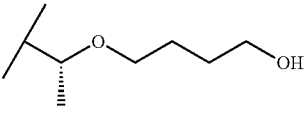 | 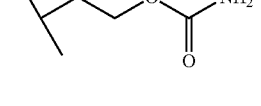 |
| 137 | O | 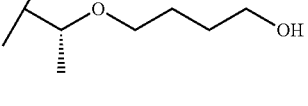 | 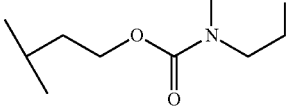 |
| 138 | O | 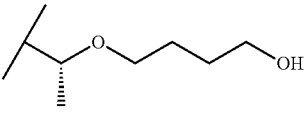 | 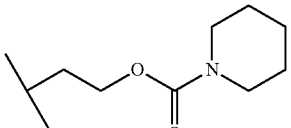 |
| 139 | O | 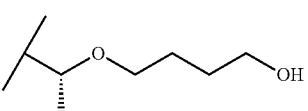 | 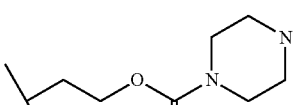 |
| 140 | | 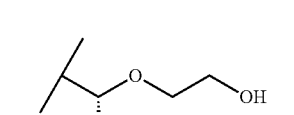 | H |
| 141 | O | 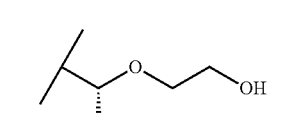 | H |
| 142 | O | 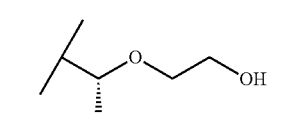 | Ac |
| 143 | O | 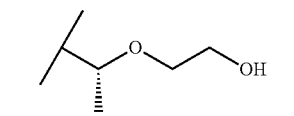 | allyl |

TABLE II-continued

| Example | W | R₄ | R₃ |
|---|---|---|---|
| 144 | O | (S)-CH(CH₃)-O-CH₂CH₂-OH | -C(CH₃)₂-C(O)NH₂ |
| 145 | O | (S)-CH(CH₃)-O-CH₂CH₂-OH | -C(CH₃)₂-C(O)N(CH₃)₂ |
| 146 | O | (S)-CH(CH₃)-O-CH₂CH₂-OH | -C(CH₃)₂-C(O)N(CH₂CH₃)₂ |
| 147 | O | (S)-CH(CH₃)-O-CH₂CH₂-OH | -C(CH₃)₂-C(O)-aziridin-1-yl |
| 148 | O | (S)-CH(CH₃)-O-CH₂CH₂-OH | -C(CH₃)₂-C(O)-azetidin-1-yl |
| 149 | O | (S)-CH(CH₃)-O-CH₂CH₂-OH | -C(CH₃)₂-C(O)-pyrrolidin-1-yl |
| 150 | O | (S)-CH(CH₃)-O-CH₂CH₂-OH | -C(CH₃)₂-C(O)-piperidin-1-yl |
| 151 | O | (S)-CH(CH₃)-O-CH₂CH₂-OH | -C(CH₃)₂-C(O)-morpholin-4-yl |
| 152 | O | (S)-CH(CH₃)-O-CH₂CH₂-OH | -C(CH₃)₂-C(O)-thiomorpholin-4-yl |
| 153 | O | (S)-CH(CH₃)-O-CH₂CH₂-OH | -C(CH₃)₂-C(O)-(1,1-dioxo-thiomorpholin-4-yl) |

TABLE II-continued
| Example | W | R₄ | R₃ |
|---|---|---|---|
| 154 | O | 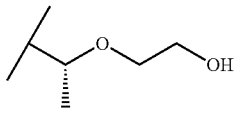 | 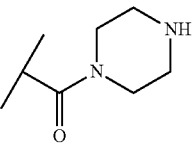 |
| 155 | O | 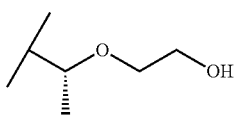 | 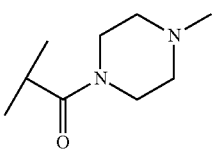 |
| 156 | O | 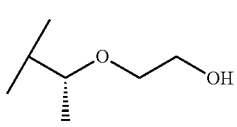 | 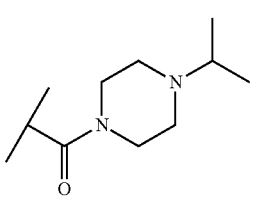 |
| 157 | O | 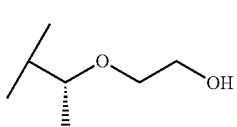 | 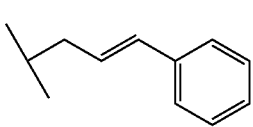 |
| 158 | O | 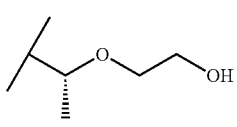 | 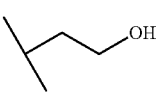 |
| 159 | O | 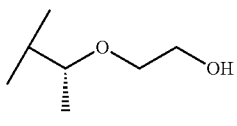 | 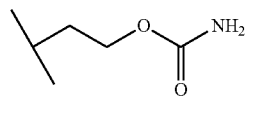 |
| 160 | O | 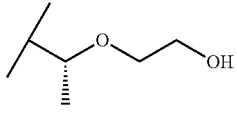 | 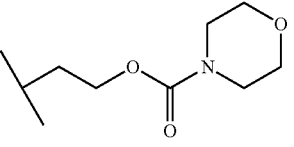 |
| 161 | O | 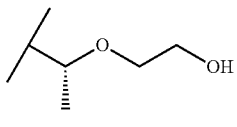 | 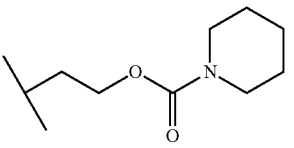 |
| 162 | O | 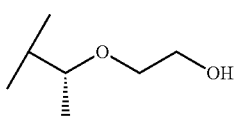 | 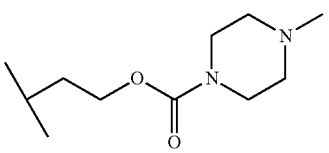 |
| 163 | | 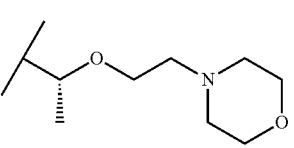 | H |

TABLE II-continued

| Example | W | R4 | R3 |
|---|---|---|---|
| 164 | O | (morpholinoethoxy-isopropyl group) | H |
| 165 | O | (morpholinoethoxy-isopropyl group) | Ac |
| 166 | O | (morpholinoethoxy-isopropyl group) | allyl |
| 167 | O | (morpholinoethoxy-isopropyl group) | -C(CH3)2-C(O)NH2 |
| 168 | O | (morpholinoethoxy-isopropyl group) | -C(CH3)2-C(O)N(CH3)2 |
| 169 | O | (morpholinoethoxy-isopropyl group) | -C(CH3)2-C(O)N(Et)2 |
| 170 | O | (morpholinoethoxy-isopropyl group) | -C(CH3)2-C(O)-aziridinyl |
| 171 | O | (morpholinoethoxy-isopropyl group) | -C(CH3)2-C(O)-azetidinyl |
| 172 | O | (morpholinoethoxy-isopropyl group) | -C(CH3)2-C(O)-pyrrolidinyl |
| 173 | O | (morpholinoethoxy-isopropyl group) | -C(CH3)2-C(O)-piperidinyl |

TABLE II-continued

| Example | W | R₄ | R₃ |
|---|---|---|---|
| 174 | O | 2-morpholinoethoxy-isopropyl | isobutyryl-morpholine |
| 175 | O | 2-morpholinoethoxy-isopropyl | isobutyryl-thiomorpholine |
| 176 | O | 2-morpholinoethoxy-isopropyl | isobutyryl-thiomorpholine 1,1-dioxide |
| 177 | O | 2-morpholinoethoxy-isopropyl | isobutyryl-piperazine |
| 178 | O | 2-morpholinoethoxy-isopropyl | isobutyryl-4-methylpiperazine |
| 179 | O | 2-morpholinoethoxy-isopropyl | isobutyryl-4-isopropylpiperazine |
| 180 | O | 2-morpholinoethoxy-isopropyl | 4-phenyl-but-3-enyl |
| 181 | O | 2-morpholinoethoxy-isopropyl | 3-methyl-4-hydroxybutyl |
| 182 | O | 2-morpholinoethoxy-isopropyl | 3-methyl-4-carbamoyloxybutyl |

TABLE II-continued

| Example | W | R₄ | R₃ |
|---|---|---|---|
| 183 | O | | |
| 184 | O | | |
| 185 | O | | |

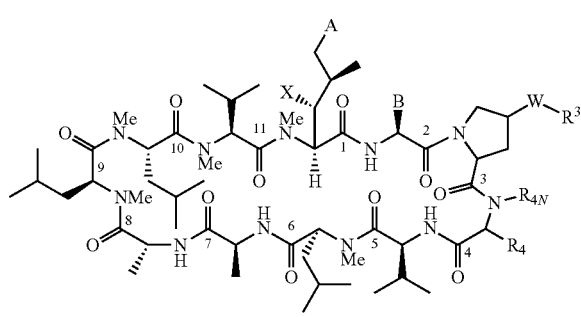

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the formula (I);

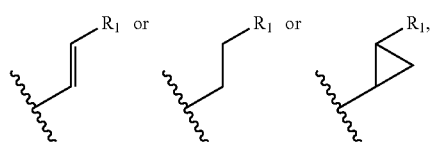

or a pharmaceutically acceptable salt thereof, where:
A is where, $R_1$ is selected from;
a) $R_{11}$, where $R_{11}$ is selected from;
  1) Hydrogen;
  2) Deuterium;
  3) $C_1$-$C_8$ alkyl;
  4) Substituted $C_1$-$C_8$ alkyl;
  5) $C_2$-$C_8$ alkenyl;
  6) Substituted $C_2$-$C_8$ alkenyl;
  7) $C_2$-$C_8$ alkynyl;
  8) Substituted $C_2$-$C_8$ alkynyl;
  9) $C_3$-$C_{12}$ cycloalkyl;
  10) Substituted $C_3$-$C_{12}$ cycloalkyl;
  11) Aryl;
  12) Substituted aryl;
  13) Heterocycloalkyl;
  14) Substituted heterocycloalkyl;
  15) Heteroaryl; and
  16) Substituted heteroaryl;
b) —C(O)OR$_{11}$, where R$_{11}$ is as previously defined;
c) —C(O)R$_{11}$, where R$_{11}$ is as previously defined;
d) —C(O)OCH$_2$—V—R$_{12}$, where V is —O— or —S— and R$_{12}$ is selected from;
  a. $C_1$-$C_8$ alkyl;
  b. Substituted $C_1$-$C_8$ alkyl;
  c. $C_2$-$C_8$ alkenyl;
  d. Substituted $C_2$-$C_8$ alkenyl;
  e. $C_2$-$C_8$ alkynyl;
  f. Substituted $C_2$-$C_8$ alkynyl;
  g. $C_3$-$C_{12}$ cycloalkyl;
  h. Substituted $C_3$-$C_{12}$ cycloalkyl;
  i. Aryl;
  j. Substituted aryl;
  k. Heterocycloalkyl;
  l. Substituted heterocycloalkyl;
  m. Heteroaryl; and
  n. Substituted heteroaryl;
e) —C(O)N(R$_{13}$)(R$_{14}$), where R$_{13}$ and R$_{14}$ are independently selected from R$_{11}$ and R$_{11}$ is as previously defined or R$_{13}$ and R$_{14}$ taken together with the nitrogen atom to which they are attached form a substituted or unsubstituted heterocycloalkyl;
f) —C(O)SR$_{11}$, where R$_{11}$ is as previously defined;
g) —C(S)OR$_{11}$, where R$_{11}$ is as previously defined;
h) —C(O)OCH$_2$OC(O)R$_{12}$, where R$_{12}$ is as previously defined;
i) —C(S)SR$_{11}$, where R$_{11}$ is as previously defined; and j) $R_{15}$, where $R_{15}$ is selected from;
  a. -M-$R_{11}$, where $R_{11}$ is as previously defined and M is selected from;
    i. $C_1$-$C_8$ alkyl;
    ii. Substituted $C_1$-$C_8$ alkyl;
    iii. $C_2$-$C_8$ alkenyl;
    iv. Substituted $C_2$-$C_8$ alkenyl;
    v. $C_2$-$C_8$ alkynyl;
    vi. Substituted $C_2$-$C_8$ alkynyl;
    vii. $C_3$-$C_{12}$ cycloalkyl; and
    viii. Substituted $C_3$-$C_{12}$ cycloalkyl;
  b. -M-$NR_{13}R_{14}$, where $R_{13}$, $R_{14}$ and M are as previously defined;
  c. -M-$S(O)_m R_{11}$, where m=0, 1, or 2; M and $R_{11}$ are as previously defined;
  d. -M-$OR_{11}$, where M and $R_{11}$ are as previously defined;
  e. -M-$C(O)R_{11}$, where M and $R_{11}$ are as previously defined;
  f. -M-$OC(O)R_{12}$, where M and $R_{12}$ are as previously defined;
  g. -M-$OC(O)OR_{12}$, where M and $R_{12}$ are as previously defined;
  h. -M-$NR_{17}C(O)R_{12}$, where $R_{17}$ is $R_{11}$, M and $R_{12}$ are as previously defined;
  i. -$MNR_{17}C(O)OR_{12}$, where $R_{17}$, M and $R_{12}$ are as previously defined;
  j. -M-$C(O)NR_{13}R_{14}$, where $R_{13}$, M and $R_{14}$ are as previously defined;
  k. -M-$C(O)N(R_{17})$—$OR_{11}$, where $R_{17}$, M and $R_{11}$ are as previously defined;
  l. -M-$OC(O)NR_{13}R_{14}$, where $R_{13}$, M and $R_{14}$ are as previously defined;
  m. -M-$NR_{17}C(O)NR_{13}R_{14}$, where M, $R_{13}$, $R_{17}$ and $R_{14}$ are as previously defined;
  n. -M-$C(S)SR_{11}$, where M and $R_{11}$ are as previously defined;
  o. -M-$OC(S)SR_{12}$, where M and $R_{12}$ are as previously defined;
  p. -M-$NR_{17}C(O)SR_{12}$, where M, $R_{17}$ and $R_{12}$ are as previously defined;
  q. -M-$SC(O)NR_{13}R_{14}$, where M, $R_{13}$ and $R_{14}$ are as previously defined;
  r. -M-CH=N—$OR_{11}$, where M and $R_{11}$ are as previously defined; and
  s. -M-CH=N—$NR_{13}R_{14}$, where M, $R_{13}$ and $R_{14}$ are as previously defined;

B is ethyl, 1-hydroxyethyl, isopropyl or n-propyl;
X is $OR_1$ or $SR_1$, where $R_1$ is as previously defined;
W is absent, —O— or —$S(O)_m$—, where m=0, 1 or 2;
$R_3$ is $R_1$, where $R_1$ is as previously defined;
$R_{4N}$ is selected from methyl, ethyl, allyl and propyl; and
$R_4$ is —$(CH_2)n_1$-$C(R_{41})(R_{42})$—$W_1$—$R_1$, where $n_1$=0, 1 or 2; $W_1$ is absent, —O—, or —$S(O)_m$—, where m=0, 1 or 2; $R_{41}$ and $R_{42}$ are independently selected from: hydrogen, methyl, ethyl, allyl, propyl or isopropyl; and $R_1$ is as previously defined.

2. A compound according to claim 1 which is represented by the formula (II);

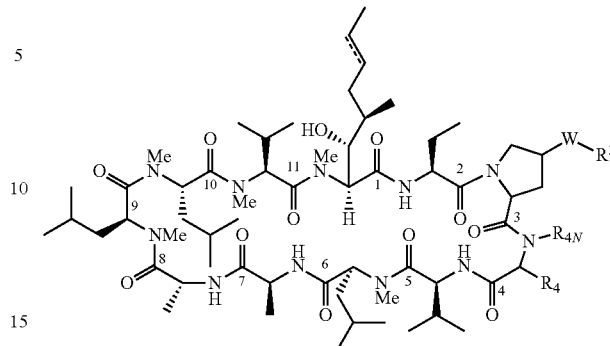

or a pharmaceutically acceptable salt thereof, wherein, $R_3$, $R_4$, $R_{4N}$, and W are as defined in claim 1 and ≡≡≡ represents a single bond or a double bond.

3. A compound according to claim 1 which is represented by the formula (III);

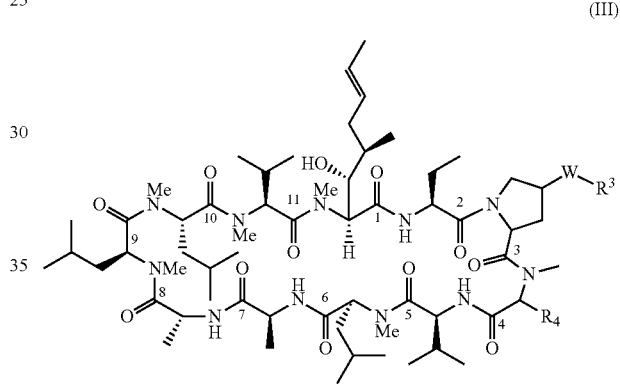

or a pharmaceutically acceptable salt thereof, wherein, $R_3$, $R_4$ and W are as defined in claim 1.

4. A compound according to claim 1 which is represented by the formula (IV);

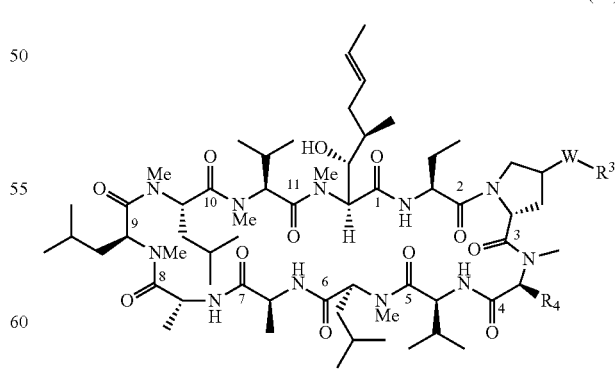

or a pharmaceutically acceptable salt thereof, wherein $R_3$, $R_4$ and W are as defined in claim 1.

5. A compound according to claim 4 which is selected from the group consisting of:

Example 1: Compound of formula IV: $R_4$=isobutyl, W is absent, and $R_3$=H;
Example 2: Compound of formula IV: $R_4$=isobutyl, W=O, and $R_3$=H;
Example 3: Compound of formula IV: $R_4$=isobutyl, W=O, and $R_3$=Me;
Example 4: Compound of formula IV: $R_4$=isobutyl, W=O, and $R_3$=Ac;
Example 5: Compound of formula IV: $R_4$=isobutyl, W=O, and $R_3$=allyl;
Example 6: Compound of formula IV: $R_4$=isobutyl, W=O, and $R_3$=—C(O)NH$_2$;
Example compounds 7-24 of the formula IV, wherein W, $R_4$ and $R_3$ are delineated for each example in Table I:

TABLE I

| Example | W | $R_4$ | $R_3$ |
|---|---|---|---|
| 7 | O | isobutyl | N,N-dimethylamide |
| 8 | O | isobutyl | N,N-diethylamide |
| 9 | O | isobutyl | aziridinyl carbonyl |
| 10 | O | isobutyl | azetidinyl carbonyl |
| 11 | O | isobutyl | pyrrolidinyl carbonyl |
| 12 | O | isobutyl | piperidinyl carbonyl |
| 13 | O | isobutyl | morpholinyl carbonyl |
| 14 | O | isobutyl | thiomorpholinyl carbonyl |
| 15 | O | isobutyl | thiomorpholinyl-S,S-dioxide carbonyl |
| 16 | O | isobutyl | piperazinyl carbonyl |
| 17 | O | isobutyl | 4-methylpiperazinyl carbonyl |
| 18 | O | isobutyl | 4-isopropylpiperazinyl carbonyl |
| 19 | O | isobutyl | cinnamyl |
| 20 | O | isobutyl | hydroxyethyl |
| 21 | O | isobutyl | carbamate (OC(O)NH$_2$) |
| 22 | O | isobutyl | morpholinyl carbamate |
| 23 | O | isobutyl | piperidinyl carbamate |
| 24 | O | isobutyl | 4-methylpiperazinyl carbamate | and

Example compounds 25-185 of the formula IV, wherein W, $R_4$ and $R_3$ are delineated for each example in Table II:

TABLE II

| Example | W | $R_4$ | $R_3$ |
|---|---|---|---|
| 25 | absent | isopropyl | H |
| 26 | O | isopropyl | H |
| 27 | O | isopropyl | Ac |
| 28 | O | isopropyl | allyl |
| 29 | O | isopropyl | C(=O)NH$_2$ (isopropyl-C(O)NH$_2$) |
| 30 | O | isopropyl | C(=O)N(CH$_3$)$_2$ |
| 31 | O | isopropyl | C(=O)N(Et)$_2$ |
| 32 | O | isopropyl | C(=O)-aziridinyl |
| 33 | O | isopropyl | C(=O)-azetidinyl |
| 34 | O | isopropyl | C(=O)-pyrrolidinyl |

TABLE II-continued

| Example | W | R₄ | R₃ |
|---|---|---|---|
| 35 | O | isobutyl | 1-(piperidin-1-yl)-2-methylpropan-1-one |
| 36 | O | isobutyl | 1-(morpholin-4-yl)-2-methylpropan-1-one |
| 37 | O | isobutyl | 1-(thiomorpholin-4-yl)-2-methylpropan-1-one |
| 38 | O | isobutyl | 1-(1,1-dioxothiomorpholin-4-yl)-2-methylpropan-1-one |
| 39 | O | isobutyl | 1-(piperazin-1-yl)-2-methylpropan-1-one |
| 40 | O | isobutyl | 1-(4-methylpiperazin-1-yl)-2-methylpropan-1-one |
| 41 | O | isobutyl | 1-(4-isopropylpiperazin-1-yl)-2-methylpropan-1-one |
| 42 | O | isobutyl | (E)-4-phenylbut-3-en-1-yl |
| 43 | O | isobutyl | 3-hydroxypropyl |
| 44 | O | isobutyl | 3-(carbamoyloxy)propyl |

TABLE II-continued

| Example | W | R₄ | R₃ |
|---|---|---|---|
| 45 | O | isopropyl-CH< | -CH₂CH(CH₃)CH₂-O-C(O)-N(morpholine) |
| 46 | O | isopropyl-CH< | -CH₂CH(CH₃)CH₂-O-C(O)-N(piperidine) |
| 47 | O | isopropyl-CH< | -CH₂CH(CH₃)CH₂-O-C(O)-N(4-methylpiperazine) |
| 48 | absent | -CH(CH₃)CH₂OH | H |
| 49 | O | -CH(CH₃)CH₂OH | H |
| 50 | O | -CH(CH₃)CH₂OH | Ac |
| 51 | O | -CH(CH₃)CH₂OH | allyl |
| 52 | O | -CH(CH₃)CH₂OH | -CH(CH₃)C(O)NH₂ |
| 53 | O | -CH(CH₃)CH₂OH | -CH(CH₃)C(O)N(CH₃)₂ |
| 54 | O | -CH(CH₃)CH₂OH | -CH(CH₃)C(O)N(CH₂CH₃)₂ |
| 55 | O | -CH(CH₃)CH₂OH | -CH(CH₃)C(O)N(aziridine) |
| 56 | O | -CH(CH₃)CH₂OH | -CH(CH₃)C(O)N(azetidine) |

TABLE II-continued

| Example | W | R₄ | R₃ |
|---|---|---|---|
| 57 | O | isobutanol | 2-methyl-1-(pyrrolidin-1-yl)propan-1-one |
| 58 | O | isobutanol | 2-methyl-1-(piperidin-1-yl)propan-1-one |
| 59 | O | isobutanol | 2-methyl-1-morpholinopropan-1-one |
| 60 | O | isobutanol | 2-methyl-1-(thiomorpholin-4-yl)propan-1-one |
| 61 | O | isobutanol | 2-methyl-1-(1,1-dioxo-thiomorpholin-4-yl)propan-1-one |
| 62 | O | isobutanol | 2-methyl-1-(piperazin-1-yl)propan-1-one |
| 63 | O | isobutanol | 2-methyl-1-(4-methylpiperazin-1-yl)propan-1-one |
| 64 | O | isobutanol | 2-methyl-1-(4-isopropylpiperazin-1-yl)propan-1-one |
| 65 | O | isobutanol | (E)-4-phenyl-but-3-enyl |
| 66 | O | isobutanol | 3-methyl-butan-1-ol |

TABLE II-continued
| Example | W | R4 | R3 |
|---|---|---|---|
| 67 | O | 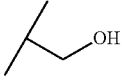 | 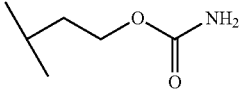 |
| 68 | O | 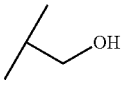 | 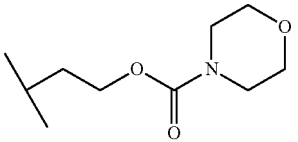 |
| 69 | O | 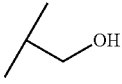 | 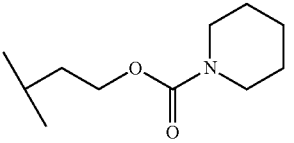 |
| 70 | O | 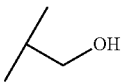 | 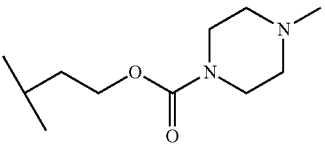 |
| 71 | absent | 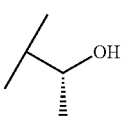 | H |
| 72 | O | 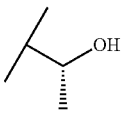 | H |
| 73 | O | 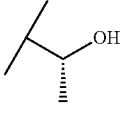 | Ac |
| 74 | O | 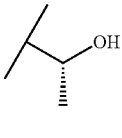 | allyl |
| 75 | O | 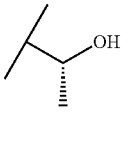 | 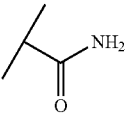 |
| 76 | O | 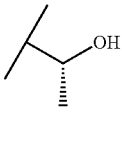 | 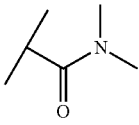 |
| 77 | O | 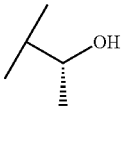 | 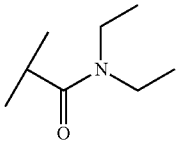 |

TABLE II-continued

| Example | W | R₄ | R₃ |
|---|---|---|---|
| 78 | O | CH(CH₃)-CH(OH)- (R configuration) | isobutyryl-aziridine |
| 79 | O | CH(CH₃)-CH(OH)- | isobutyryl-azetidine |
| 80 | O | CH(CH₃)-CH(OH)- | isobutyryl-pyrrolidine |
| 81 | O | CH(CH₃)-CH(OH)- | isobutyryl-piperidine |
| 82 | O | CH(CH₃)-CH(OH)- | isobutyryl-morpholine |
| 83 | O | CH(CH₃)-CH(OH)- | isobutyryl-thiomorpholine |
| 84 | O | CH(CH₃)-CH(OH)- | isobutyryl-thiomorpholine 1,1-dioxide |
| 85 | O | CH(CH₃)-CH(OH)- | isobutyryl-piperazine |
| 86 | O | CH(CH₃)-CH(OH)- | isobutyryl-4-methylpiperazine |
| 87 | O | CH(CH₃)-CH(OH)- | isobutyryl-4-isopropylpiperazine |

TABLE II-continued

| Example | W | R₄ | R₃ |
|---|---|---|---|
| 88 | O | CH(CH₃)CH(OH)CH₃ | CH₂CH=CH-phenyl |
| 89 | O | CH(CH₃)CH(OH)CH₃ | CH₂CH₂CH₂OH (with methyl branch) |
| 90 | O | CH(CH₃)CH(OH)CH₃ | CH₂CH₂CH₂-O-C(=O)-NH₂ (with methyl branch) |
| 91 | O | CH(CH₃)CH(OH)CH₃ | CH₂CH₂CH₂-O-C(=O)-morpholine (with methyl branch) |
| 92 | O | CH(CH₃)CH(OH)CH₃ | CH₂CH₂CH₂-O-C(=O)-piperidine (with methyl branch) |
| 93 | O | CH(CH₃)CH(OH)CH₃ | CH₂CH₂CH₂-O-C(=O)-N-methylpiperazine (with methyl branch) |
| 94 | absent | CH(CH₃)-O-CH₂CH=CH₂ | H |
| 95 | O | CH(CH₃)-O-CH₂CH=CH₂ | H |
| 96 | O | CH(CH₃)-O-CH₂CH=CH₂ | Ac |
| 97 | O | CH(CH₃)-O-CH₂CH=CH₂ | allyl |
| 98 | O | CH(CH₃)-O-CH₂CH=CH₂ | C(CH₃)(C(=O)NH₂) |

TABLE II-continued

| Example | W | R₄ | R₃ |
|---|---|---|---|
| 99 | O | (S)-CH(CH₃)-O-CH₂-CH=CH₂ | -C(CH₃)-C(=O)-N(CH₃)₂ |
| 100 | O | (S)-CH(CH₃)-O-CH₂-CH=CH₂ | -C(CH₃)-C(=O)-N(Et)₂ |
| 101 | O | (S)-CH(CH₃)-O-CH₂-CH=CH₂ | -C(CH₃)-C(=O)-aziridin-1-yl |
| 102 | O | (S)-CH(CH₃)-O-CH₂-CH=CH₂ | -C(CH₃)-C(=O)-azetidin-1-yl |
| 103 | O | (S)-CH(CH₃)-O-CH₂-CH=CH₂ | -C(CH₃)-C(=O)-pyrrolidin-1-yl |
| 104 | O | (S)-CH(CH₃)-O-CH₂-CH=CH₂ | -C(CH₃)-C(=O)-piperidin-1-yl |
| 105 | O | (S)-CH(CH₃)-O-CH₂-CH=CH₂ | -C(CH₃)-C(=O)-morpholin-4-yl |
| 106 | O | (S)-CH(CH₃)-O-CH₂-CH=CH₂ | -C(CH₃)-C(=O)-thiomorpholin-4-yl |
| 107 | O | (S)-CH(CH₃)-O-CH₂-CH=CH₂ | -C(CH₃)-C(=O)-(1,1-dioxo-thiomorpholin-4-yl) |
| 108 | O | (S)-CH(CH₃)-O-CH₂-CH=CH₂ | -C(CH₃)-C(=O)-piperazin-1-yl |

TABLE II-continued

| Example | W | R₄ | R₃ |
|---|---|---|---|
| 109 | O | CH(CH₃)-O-CH₂-CH=CH₂ | C(=O)-N(piperazine)-N-CH₃ |
| 110 | O | CH(CH₃)-O-CH₂-CH=CH₂ | C(=O)-N(piperazine)-N-iPr |
| 111 | O | CH(CH₃)-O-CH₂-CH=CH₂ | CH₂-CH=CH-Ph |
| 112 | O | CH(CH₃)-O-CH₂-CH=CH₂ | CH₂CH₂OH |
| 113 | O | CH(CH₃)-O-CH₂-CH=CH₂ | CH₂CH₂-O-C(=O)-NH₂ |
| 114 | O | CH(CH₃)-O-CH₂-CH=CH₂ | CH₂CH₂-O-C(=O)-N(morpholine) |
| 115 | O | CH(CH₃)-O-CH₂-CH=CH₂ | CH₂CH₂-O-C(=O)-N(piperidine) |
| 116 | O | CH(CH₃)-O-CH₂-CH=CH₂ | CH₂CH₂-O-C(=O)-N(piperazine)-N-CH₃ |
| 117 | absent | CH(CH₃)-O-CH₂CH₂CH₂CH₂-OH | H |
| 118 | O | CH(CH₃)-O-CH₂CH₂CH₂CH₂-OH | H |
| 119 | O | CH(CH₃)-O-CH₂CH₂CH₂CH₂-OH | Ac |

TABLE II-continued

| Example | W | R$_4$ | R$_3$ |
|---|---|---|---|
| 120 | O | –CH(CH$_3$)–O–(CH$_2$)$_4$–OH | allyl |
| 121 | O | –CH(CH$_3$)–O–(CH$_2$)$_4$–OH | –C(CH$_3$)$_2$–C(O)NH$_2$ |
| 122 | O | –CH(CH$_3$)–O–(CH$_2$)$_4$–OH | –C(CH$_3$)$_2$–C(O)N(CH$_3$)$_2$ |
| 123 | O | –CH(CH$_3$)–O–(CH$_2$)$_4$–OH | –C(CH$_3$)$_2$–C(O)N(CH$_2$CH$_3$)$_2$ |
| 124 | O | –CH(CH$_3$)–O–(CH$_2$)$_4$–OH | –C(CH$_3$)$_2$–C(O)-aziridin-1-yl |
| 125 | O | –CH(CH$_3$)–O–(CH$_2$)$_4$–OH | –C(CH$_3$)$_2$–C(O)-azetidin-1-yl |
| 126 | O | –CH(CH$_3$)–O–(CH$_2$)$_4$–OH | –C(CH$_3$)$_2$–C(O)-pyrrolidin-1-yl |
| 127 | O | –CH(CH$_3$)–O–(CH$_2$)$_4$–OH | –C(CH$_3$)$_2$–C(O)-piperidin-1-yl |
| 128 | O | –CH(CH$_3$)–O–(CH$_2$)$_4$–OH | –C(CH$_3$)$_2$–C(O)-morpholin-4-yl |
| 129 | O | –CH(CH$_3$)–O–(CH$_2$)$_4$–OH | –C(CH$_3$)$_2$–C(O)-thiomorpholin-4-yl |

TABLE II-continued
| Example | W | R₄ | R₃ |
|---|---|---|---|
| 130 | O | 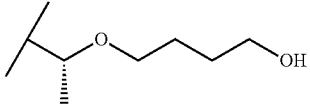 | 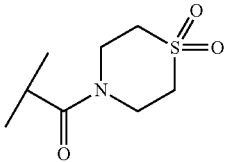 |
| 131 | O | 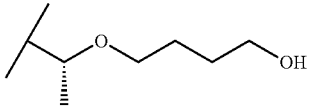 | 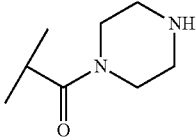 |
| 132 | O | 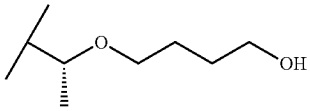 | 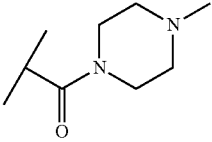 |
| 133 | O | 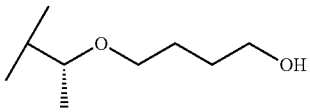 | 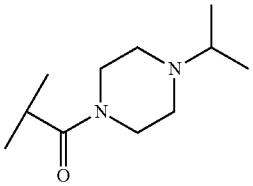 |
| 134 | O | 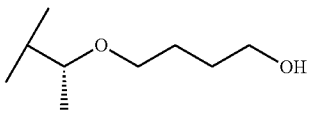 | 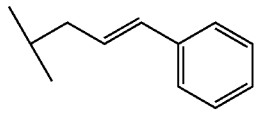 |
| 135 | O | 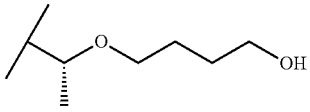 | 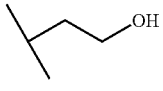 |
| 136 | O | 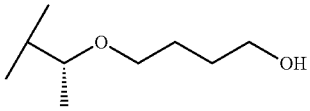 | 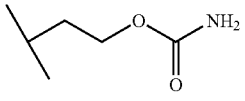 |
| 137 | O | 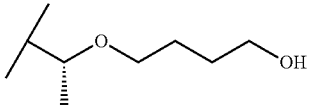 | 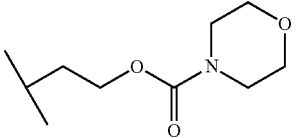 |
| 138 | O | 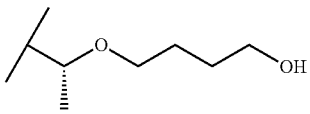 | 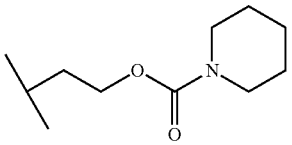 |
| 139 | O | 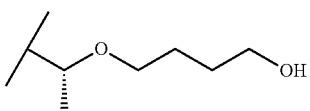 | 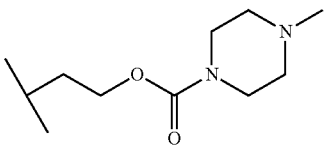 |

TABLE II-continued
| Example | W | R₄ | R₃ |
|---|---|---|---|
| 140 | absent | 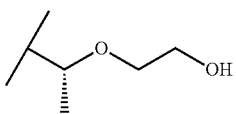 | H |
| 141 | O | 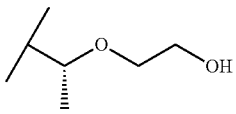 | H |
| 142 | O | 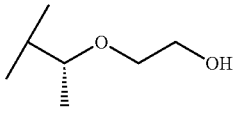 | Ac |
| 143 | O | 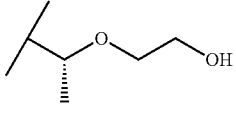 | allyl |
| 144 | O | 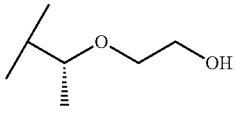 | 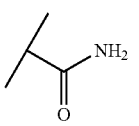 |
| 145 | O | 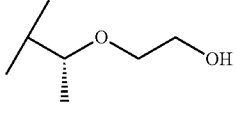 | 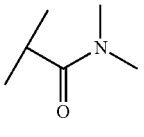 |
| 146 | O | 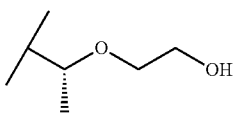 | 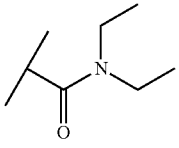 |
| 147 | O | 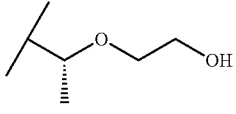 | 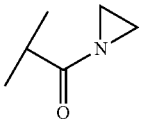 |
| 148 | O | 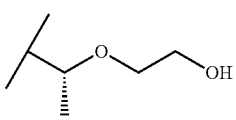 | 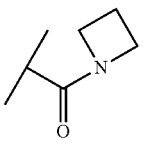 |
| 149 | O | 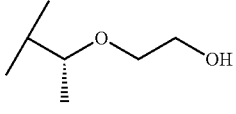 | 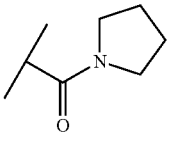 |
| 150 | O | 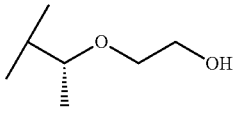 | 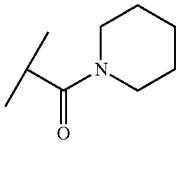 |

TABLE II-continued

| Example | W | R₄ | R₃ |
|---|---|---|---|
| 151 | O | (S)-1-methyl-2-(2-hydroxyethoxy)ethyl | morpholin-4-yl isobutyryl |
| 152 | O | (S)-1-methyl-2-(2-hydroxyethoxy)ethyl | thiomorpholin-4-yl isobutyryl |
| 153 | O | (S)-1-methyl-2-(2-hydroxyethoxy)ethyl | 1,1-dioxo-thiomorpholin-4-yl isobutyryl |
| 154 | O | (S)-1-methyl-2-(2-hydroxyethoxy)ethyl | piperazin-1-yl isobutyryl |
| 155 | O | (S)-1-methyl-2-(2-hydroxyethoxy)ethyl | 4-methyl-piperazin-1-yl isobutyryl |
| 156 | O | (S)-1-methyl-2-(2-hydroxyethoxy)ethyl | 4-isopropyl-piperazin-1-yl isobutyryl |
| 157 | O | (S)-1-methyl-2-(2-hydroxyethoxy)ethyl | (E)-4-phenyl-but-3-enyl |
| 158 | O | (S)-1-methyl-2-(2-hydroxyethoxy)ethyl | 3-hydroxy-2-methylpropyl |
| 159 | O | (S)-1-methyl-2-(2-hydroxyethoxy)ethyl | carbamate ester |
| 160 | O | (S)-1-methyl-2-(2-hydroxyethoxy)ethyl | morpholine-4-carboxylate ester |

TABLE II-continued

| Example | W | R₄ | R₃ |
|---|---|---|---|
| 161 | O | (S)-1-methyl-2-(2-hydroxyethoxy)ethyl | 3-methyl-3-(piperidine-1-carbonyloxy)butyl |
| 162 | O | (S)-1-methyl-2-(2-hydroxyethoxy)ethyl | 3-methyl-3-(4-methylpiperazine-1-carbonyloxy)butyl |
| 163 | absent | (S)-1-methyl-2-(2-morpholinoethoxy)ethyl | H |
| 164 | O | (S)-1-methyl-2-(2-morpholinoethoxy)ethyl | H |
| 165 | O | (S)-1-methyl-2-(2-morpholinoethoxy)ethyl | Ac |
| 166 | O | (S)-1-methyl-2-(2-morpholinoethoxy)ethyl | allyl |
| 167 | O | (S)-1-methyl-2-(2-morpholinoethoxy)ethyl | 2-methyl-2-carbamoylpropyl (isobutyramide) |
| 168 | O | (S)-1-methyl-2-(2-morpholinoethoxy)ethyl | N,N-dimethyl isobutyramide |
| 169 | O | (S)-1-methyl-2-(2-morpholinoethoxy)ethyl | N,N-diethyl isobutyramide |
| 170 | O | (S)-1-methyl-2-(2-morpholinoethoxy)ethyl | 2-methyl-1-(aziridin-1-yl)propan-1-one |

TABLE II-continued
| Example | W | R4 | R3 |
|---|---|---|---|
| 171 | O | 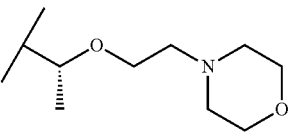 | 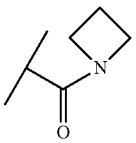 |
| 172 | O | 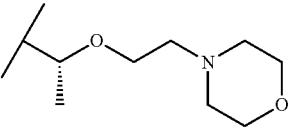 | 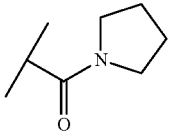 |
| 173 | O | 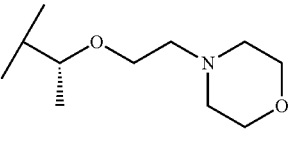 | 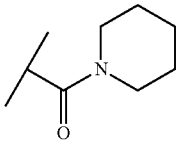 |
| 174 | O | 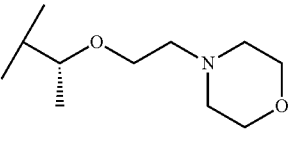 | 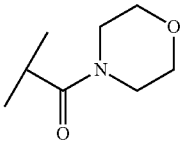 |
| 175 | O | 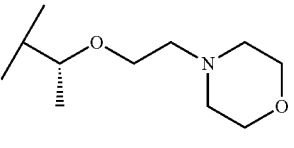 | 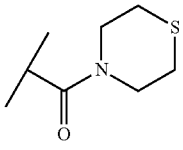 |
| 176 | O | 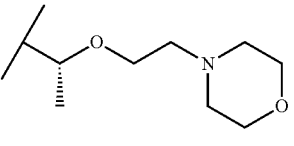 | 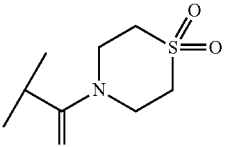 |
| 177 | O | 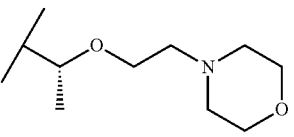 | 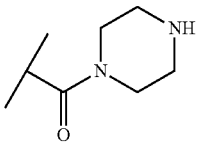 |
| 178 | O | 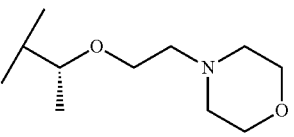 | 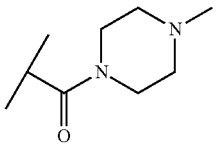 |
| 179 | O | 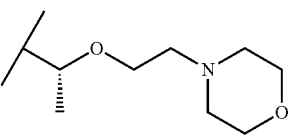 | 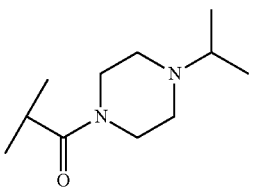 |

TABLE II-continued

| Example | W | R₄ | R₃ |
|---|---|---|---|
| 180 | O | (morpholinoethoxy group) | (styryl/cinnamyl group) |
| 181 | O | (morpholinoethoxy group) | (hydroxyalkyl group, –CH₂CH₂OH) |
| 182 | O | (morpholinoethoxy group) | –CH₂CH₂O–C(=O)–NH₂ |
| 183 | O | (morpholinoethoxy group) | –CH₂CH₂O–C(=O)–N(morpholine) |
| 184 | O | (morpholinoethoxy group) | –CH₂CH₂O–C(=O)–N(piperidine) |
| 185 | O | (morpholinoethoxy group) | –CH₂CH₂O–C(=O)–N(N-methylpiperazine) | or a pharmaceutically acceptable salt thereof.

6. A pharmaceutical composition comprising a therapeutically effective amount of a compound of claim 1 or a pharmaceutically-acceptable salt, ester or prodrug thereof, in combination with a pharmaceutically acceptable carrier.

7. A method of treating organ transplantation rejection in a subject, which comprises administering to said subject a therapeutically effective amount of the pharmaceutical composition of claim 6.

8. A method of treating an immune disorder in a subject, which comprises administering to said subject a therapeutically effective amount of the pharmaceutical composition of claim 6.

9. The method of claim 8, wherein said immune disorder is selected from the group consisting of psoriasis and eczema.

10. The method of claim 9, wherein said administering is topical.

11. The method of claim 8, wherein said immune disorder is selected from the group consisting of: rheumatoid arthritis, inflammatory bowel disease, psoriasis, asthma, allergic rhinitis and chronic obstructive pulmonary disease.

12. A method of treating inflammatory or obstructive airway disease in a subject in need of said treatment, comprising topically administering to said subject a therapeutically effective amount of the pharmaceutical composition as defined in claim 6.

13. The method of claim 12, wherein said topically administering is by inhalation.

14. The method of claim 12, wherein said airways disease is selected from the group consisting of asthma, allergic rhinitis, bronchitis, chronic obstructive pulmonary disease, chronic bronchitis and cystic fibrosis.

15. A method of treating a viral infection in a subject in need thereof, comprising administering to said subject a therapeutically-effective amount of a pharmaceutical composition of claim 6.

16. The method according to claim 15 wherein said viral infection is selected from HCV, HBV, HAV and HIV infection.

17. The method of claim 16 further comprising coadministering one or more additional anti-viral agents.

18. The method of claim 17 wherein said one or more additional anti-viral agents are selected from 1) peg-interferon and ribavirin, 2) viral-enzyme targeted compounds, 3) viral-genome-targeted therapies, and 4) immunomodulatory agents.

* * * * *